US008586329B2

(12) United States Patent
Hofmann et al.

(10) Patent No.: US 8,586,329 B2
(45) Date of Patent: Nov. 19, 2013

(54) NEUROTOXINS EXHIBITING SHORTENED BIOLOGICAL ACTIVITY

(75) Inventors: Fred Hofmann, Potsdam (DE); Jurgen Frevert, Berlin (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/381,533

(22) PCT Filed: Jul. 1, 2010

(86) PCT No.: PCT/EP2010/059398
§ 371 (c)(1),
(2), (4) Date: Dec. 29, 2011

(87) PCT Pub. No.: WO2011/000929
PCT Pub. Date: Jan. 6, 2011

(65) Prior Publication Data
US 2012/0107362 A1    May 3, 2012

Related U.S. Application Data

(60) Provisional application No. 61/270,198, filed on Jul. 2, 2009.

(30) Foreign Application Priority Data

Jul. 2, 2009 (EP) .................................... 09164365

(51) Int. Cl.
*C12P 21/06* (2006.01)
*C07H 21/04* (2006.01)
*A61K 39/08* (2006.01)

(52) U.S. Cl.
USPC ...................... 435/69.1; 424/247.1; 536/23.7

(58) Field of Classification Search
None
See application file for complete search history.

(56) References Cited

U.S. PATENT DOCUMENTS 7,172,764 B2 *   2/2007   Li et al. ....................... 424/239.1
7,211,261 B1    5/2007   Moyer et al.

FOREIGN PATENT DOCUMENTS

WO    WO 2005/007185    1/2005
WO    WO 2006/020208    2/2006

OTHER PUBLICATIONS

Belizario, Science vol. 9, p. 210-220, 2008.
Chen, Infect Immuni, vol. 66, No. 6, p. 2420-2425, 1998.
Couesnon, Microbiology, vol. 152, p. 759-770, 2006.
Dasgupta Bibhuti, R. The Journal of General and Applied Microbiology, vol. 54, No. 1, p. 1-8, Feb. 1, 2006.
Dressler, Mov. Disorder, vol. 20, p. 1617-1619, 2005.
Eleopra, Neurosci Lett. 13, vol. 256, No. 3, p. 135-138, 1998.
Eleopra, Neurosci Lett. 14, vol. 224, No. 2, Pt 91-94, 1997.
European Search Report for EP09164365 of Aug. 11, 2009.
Falnes, P.O., et al, EMBO Journal, vol. 17, No. 2, p. 615-625, Jan. 1, 1998.
Fischer, PNAS, vol. 104, p. 10447-10452, 2007.
Foran, J. Biol. Chem., vol. 278, No. 2, p. 1363-1371, 2003.
Gupta Pradeep K, et al. PLOS One 2008: vol. 3, No. 9, p. E3130, Jan. 1. 2008.
Ibanez, C., et al., FEBS Letters, vol. 578, No. 1-2, p. 121-127, Dec. 3, 2004.
International Preliminary Report on Patentability for PCT/EP2010/059398 of Jan. 12, 2012.
International Search Report for PCT/EP2010/059398 of Oct. 4, 2010.
Jost, Drugs, vol. 57, p. 669-683, 2007.
Keller, Neuroscience, vol. 139, p. 629-637, 2006.
Krieglstein, Eur J. Biochem, vol. 188, p. 39-45, 1990.
Krieglstein, Eur J. Biochem, vol. 202, p. 41-51, 1991.
Krieglstein, J. Protein Chem., vol. 13, p. 49-57, 1994.
Oyler, G.A., et al, Toxicon, vol. 51, p. 17, Jun. 1, 2008.
Pearce, Toxicol Appl Pharmacol, vol. 128, p. 69-77, 1994.
Rechsteiner, TIBS, vol. 21, p. 267-271, 1996.
Rogers, Science, vol. 234, p. 364-368, 1986.
Sloop, Neurology, vol. 49, No. 1, p. 189-194, 1997.
Suzuki, T., et al, EMBO Journal, vol. 18, No. 21, p. 6017-6026, Jan. 1, 1999.
Washbourne, J. Physiol Paris, vol. 92, No. 2, p. 135-139, 1998.

* cited by examiner

*Primary Examiner* — Padma V Baskar
(74) *Attorney, Agent, or Firm* — Hueschen and Sage

(57) ABSTRACT

The present invention relates to the pharmaceutical field. Specifically, it contemplates a polynucleotide encoding a neurotoxin polypeptide exhibiting a reduced duration of the biological effect in a subject, wherein the polypeptide comprises at least one degradation signal in the light chain of the neurotoxin polypeptide as well as vectors and host cells comprising the polynucleotide, polypeptides encoded thereby and antibodies specifically binding to the polypeptides. Moreover, the invention relates to medicaments comprising the polynucleotides and polypeptides, as well as specific therapeutic applications thereof. Furthermore, the present invention contemplates methods for the manufacture of the polypeptides and medicaments.

11 Claims, No Drawings

NEUROTOXINS EXHIBITING SHORTENED BIOLOGICAL ACTIVITY

The present invention relates to the pharmaceutical field. Specifically, it contemplates a polynucleotide encoding a Neurotoxin polypeptide exhibiting a reduced duration of the biological effect in a subject, wherein said polypeptide comprises at least one degradation signal in the light chain as well as vectors and host cells comprising the said polynucleotide, polypeptides encoded thereby and antibodies specifically binding to the polypeptides. Moreover, the invention relates to medicaments comprising said polynucleotides and polypeptides as well as specific therapeutic applications thereof. Furthermore, the present invention contemplates methods for the manufacture of the polypeptides and medicaments.

*Clostridium botulinum* and *Clostridium tetani* produce highly potent neurotoxins, i.e. botulinum toxins (BoNTs) and tetanus toxin (TeNT), respectively. These Clostridial Neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active Neurotoxin consists of two chains, an N-terminal light chain of approx. 50 kDa and a heavy chain of approx. 100 kDa linked by a disulfide bond. CNTs consist of three domains, i.e. the catalytic light chain, the heavy chain encompassing the translocation domain (N-terminal half) and the receptor binding domain (C-terminal half), see Krieglstein 1990, Eur J Biochem 188, 39; Krieglstein 1991, Eur J Biochem 202, 41; Krieglstein 1994, J Protein Chem 13, 49. The Botulinum Neurotoxins are synthesized as molecular complexes comprising the 150 kDa Neurotoxin protein and associated non-toxic, complexing proteins. The complex sizes differ based on the Clostridial strain and the distinct Neurotoxin serotypes ranging from 300 kDa to 900 kDa. The complexing proteins in these complexes stabilize the Neurotoxin and protect it against degradation, see Chen 1998, Infect Immun 66(6): 2420-2425.

*Clostridium botulinum* secretes seven antigenically distinct serotypes designated A to G of the botulinum neurotoxin (BoNT). All serotypes together with the related tetanus neurotoxin (TeNT) secreted by *Clostridium tetani*, are $Zn^{2+}$-endoproteases that block synaptic exocytosis by cleaving SNARE proteins, see Couesnon, 2006, Microbiology, 152, 759. CNTs cause the flaccid muscle paralysis seen in botulism, see Fischer 2007, PNAS 104, 10447.

Despite its toxic effects, Botulinum toxins have been used as therapeutic agents for a large number of diseases or disorders. Botulinum toxin serotype A was approved for human use in the United States in 1989 for the treatment of strabism, blepharospasm, and other disorders. It is commercially available as a Botulinum toxin A protein complex, for example, under the tradename BOTOX (Allergan Inc) or under the tradename DYSPORT (Ipsen Ltd). For therapeutic applications, the complex is injected directly into the muscle to be treated. At physiological pH, the toxin is released from the protein complex and the desired pharmacological effect takes place. An improved, complex-free Neurotoxin A polypeptide preparation is available under the tradename XEOMIN (Merz Pharmaceuticals GmbH). The effect of Botulinum toxin is only temporary, which is the reason why repeated administration of Botulinum toxin may be required to maintain a therapeutic effect.

The Clostridial Neurotoxins weaken voluntary muscle strength and are effective therapeutics for strabism, focal dystonia, including cervical dystonia, and benign essential blepharospasm. They have been further shown to relief hemifacial spasm, and focal spasticity, and, moreover, to be effective in a wide range of other indications, such as gastrointestinal disorders, hyperhidrosis, and cosmetic wrinkle correction, see Jost 2007, Drugs 67, 669.

However, weakening muscle strengths and contraction is also desirable for medical conditions or disease such as wound healing, immobilisation for bone and tendon fracture treatment, post surgery immobilization, specifically in connection with haemorrhoidectomy, introduction of dental implants, or hip joint replacement (endoprothesis), knee arthroplasty, ophthalmological surgery, acne, or irritable bowel disease. The Neurotoxins usually exhibit their biological effect over a time period which is longer than actually needed for efficient treatment of said diseases or conditions. A prolonged muscle paralysis is, however, detrimental or at least less preferable in the therapy of the said medical conditions or diseases. Neurotoxins exhibiting their biological effect only over the desired time period are, however, not yet available.

Accordingly, the technical problem underlying the present invention can be seen as the provision of means and methods for complying with the aforementioned needs. The technical problem is solved by the embodiments characterized in the claims and herein below.

The present invention, therefore, relates to a polynucleotide encoding a Neurotoxin polypeptide exhibiting a reduced duration of the biological effect in a subject, wherein said polypeptide comprises at least one degradation signal in the light chain.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be in an aspect a linear or circular molecule. Moreover, in addition to the nucleic acid sequences encoding the aforementioned Neurotoxin polypeptide, a polynucleotide of the present invention may comprise additional sequences required for proper transcription and/or translation such as 5" or 3"UTR sequences. The polynucleotide of the present invention encodes a modified Neurotoxin polypeptide derivable from one of the antigenically different serotypes of Botulinum Neurotoxins, i.e. BoNT/A, BoNT/B, BoNT/C1, BoNT/D, BoNT/E, BoNT/F, BoNT/G, or Tetanus Neurotoxin (TeNT). In an aspect of the present invention, the said polynucleotide comprises a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 (BoNT/E), SEQ ID NO: 11 (BoNT/F), SEQ ID NO: 13 (BoNT/G) or SEQ ID NO: 15 (TeNT). Moreover, encompassed is in an aspect a polynucleotide comprising a nucleic acid sequence encoding an amino acid sequence as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 (BoNT/E), SEQ ID NO: 12 (BoNT/F), SEQ ID NO: 14 (BoNT/G) or SEQ ID NO: 16 (TeNT). In another aspect, the said polynucleotide is a variant of the aforementioned polynucleotides comprising one or more nucleotide substitutions, deletions and/or additions which in still another aspect may result in an encoded amino acid having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 98% or at least 99% identical to the nucleic acid sequence as shown in any one of SEQ ID NOs: 1, 3, 5, 7, 9, 11, 13 or 15 or a nucleic acid sequence variant which encodes an amino acid sequence being at least 40%, at least 50%, at least 60%, at least 70%, at least 75%, at least 80%, at least 85%, at least 90%, at least 95%, at least 98% or at least 99% identical to the amino acid sequence as shown in any one of SEQ ID NOs: 2, 4, 6, 8, 10, 12, 14, or 16. The term "identical" as used herein refers to sequence identity characterized by determining the number of identical amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

In an aspect, each of the aforementioned variant polynucleotides encodes a polypeptide retaining one or more and, in another aspect, all of the biological properties of the respective Neurotoxin polypeptide, i.e. the BoNT/A, BoNT/B, BoNT/C1, BoNT/D, BoNT/E, BoNT/F, BoNT/G or Tetanus Neurotoxin (TeNT). Those of skill in the art will appreciate that full biological activity is maintained only after proteolytic activation, even though it is conceivable that the unprocessed precursor can exert some biological functions or be partially active. "Biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In vivo assays for assessing biological activity include the mouse LD50 assay and the ex vivo mouse hemidiaphragm assay as described by Pearce et al. (Pearce 1994, Toxicol Appl Pharmacol 128: 69-77) and Dressler et al. (Dressler 2005, Mov Disord 20:1617-1619, Keller 2006, Neuroscience 139: 629-637). The biological activity is commonly expressed in Mouse Units (MU). As used herein, 1 MU is the amount of neurotoxic component, which kills 50% of a specified mouse population after intraperitoneal injection, i.e. the mouse i.p. LD50. In a further aspect, the variant polynucleotides can encode Neurotoxins having improved or altered biological properties, e.g., they may comprise cleavage sites which are improved for enzyme recognition or may be improved for receptor binding or any other property specified above. Moreover, encompassed are in an aspect fusion polypeptides further comprising detectable marker peptides or tags. In an aspect, suitable tags are FLAG-tags, Myc-tags or His-tags which also allow for a more efficient purification of the tagged polypeptides. Detectable marker peptides, in an aspect, include fluorescent proteins such as GFP, BFP and the like. In yet a further aspect, the variant polynucleotides shall encode fusion Neurotoxin polypeptides comprising a part of at least two Neurotoxin polypeptides of different serotypes, e.g., a fusion Neurotoxin comprising a heavy chain of BoNT/A and a light chain of BoNT/E.

The Neurotoxin polypeptide encoded by the polynucleotide of the invention further comprises at least one degradation signal in its light chain. In an aspect of the invention, the said light chain of the Neurotoxin polypeptide encoded by the polynucleotide of the invention is obtained by modification from a light chain being encoded by a polynucleotide comprising any one of the aforementioned specific nucleic acid sequences or variants thereof described above. The light chains of the Neurotoxin polypeptides are generated by proteolytic cleavage of a precursor polypeptide (single-chain polypeptide). The light chain is the N-terminal portion of the precursor polypeptide which is obtained as a result of the proteolytic cleavage. The amino acid sequences of the light chains of the Neurotoxin polypeptides referred to above can be deduced, in an aspect, from the cleavage sites indicated in the following table.

TABLE 2

| Neurotoxin (Bacterial Strain) | Accession number | Cleavage site | Sequence including cleavage sites (highlighted) |
|---|---|---|---|
| BoNT/A (Hall/62A) | ABD 65472 | K428/T429 K448/A449 | KLLCVRGIITSKTKSLDKGYNKALN....DLCIKV (SEQ ID NO: 17) |
| BoNT/B (Okra) | BAE 48264 | K441/A442 | IQMCKSVKAPG...................ICIDV (SEQ ID NO: 18) |
| BoNT/C1 (C-6814) | BAA 89713 | R444/S445 K449/T450 | TKFCHKAIDGRSL....YNKTL......DCRELLV (SEQ ID NO: 19) |
| BoNT/D | BAA 90661 | K442/N443 R445/D446 | TKVCLRLTK.........NSRD......DSTCIKV (SEQ ID NO: 20) |
| BoNT/E (Beluga) | CAA 43999 | K419/G420 R422/K423 | IRFCKNIVSVKG......IRK........SICIEI (SEQ ID NO: 21) |
| BoNT/F (NCTC10281) | CAA 73972 | R435/K436 K439/A440 | VKFCKSVIPRKG......TKAP......PRLCIRV (SEQ ID NO: 22) |
| BoNT/G | CAA 52275 | | IAMCKPVMYKNT......GKS........EQCIIV (SEQ ID NO: 23) |

TABLE 2-continued

| Neurotoxin (Bacterial Strain) | Accession number | Cleavage site | Sequence including cleavage sites (highlighted) |
|---|---|---|---|
| TeNT | P 04958 | R449 (R455) | IGLCKKIIPPTNIRENLYNRTASLTDLGGELCIKI (SEQ ID NO: 24) |

The term "degradation signal" as used herein refers to modifications of the light chain of the Neurotoxin polypeptide which result in increased degradation of the Neurotoxin polypeptide by endogenous degradation pathways present in an organism to which the Neurotoxin has been applied. In an aspect, the degradation pathway will be a proteasomal degradation pathway or a lysosomal degradation pathway. In another aspect, a degradation pathway may merely result in a partial degradation of the Neurotoxin polypeptide, e.g., by one or more proteolytic cleavage steps. The said degradation signal may be introduced into the light chain (i.e. be located (internally) within the light chain) or linked thereto either N- or C-terminally. The person skilled in the art is well aware of suitable degradation signals and how to introduce or link them to the Neurotoxin polypeptide's light chain. Moreover, the skilled artisan can generate polynucleotides encoding such Neurotoxin polypeptides with the at feast one degradation signal by applying recombinant molecular biological techniques or chemical modifications. For example, site directed mutagenesis may be used for introducing the degradation signals referred to below. Alternatively, a nucleic acid sequence for the polynucleotide comprising the coding sequences for the Neurotoxin polypeptide and the envisaged degradation signal may be designed and the entire polynucleotide may subsequently be chemically synthesised.

In an aspect, the said degradation signal is selected from the group consisting of:
a) at least one internally or terminally introduced PEST motif,
b) at least one internally or terminally introduced E3 ligase recognition motif,
c) an N-terminal oligo-lysine residue,
d) an N-terminally linked ubiquitin,
e) a substitution of the N-terminal proline with a basic amino acid,
f) substitutions of surface displayed amino acid residues by lysines, and
g) a substitution of the N-terminal proline with a basic amino acid in combination with substitutions of surface displayed amino acid residues by lysines.

In an aspect, the E3 ligase recognition motif has a consensus sequence as shown in the following table (wherein "X" may represent any of the naturally occurring amino acids):

TABLE 2

| E3 ubiquitin Ligase | Recognition motif (consensus) | |
|---|---|---|
| VBCCul2 | ALAPYIP | (SEQ ID NO: 25) |
| MNM2 | RFMDYWEGL | (SEQ ID NO: 26) |
| | FXXXLWXXL | (SEQ ID NO: 27) |
| Smurf2 | ELESPPPPYSRYPM | (SEQ ID NO: 28) |
| RN181 | KVGFFKR | (SEQ ID No: 29) |
| E3alpha | LLVRGRTLVV | (SEQ ID NO 30) |

TABLE 2-continued

| E3 ubiquitin Ligase | Recognition motif (consensus) | |
|---|---|---|
| SCF | DRHDSGLDSM | (SEQ ID NO: 31) |
| Siah | PXAXVXP | (SEQ ID NO: 32) |
| Itch | PPXYXXM | (SEQ ID NO: 33) |
| Nedd4-2 | PPXY | (SEQ ID No: 34) |

PEST motifs are well known in the art as degradation signals (Rogers 1986, Science 234: 364-368, Rechsteiner 1996, TIBS 21: 267-271, Belizario 2008, Science 9: 210-220). In an aspect, the PEST motif is has a sequence as disclosed in Rechsteiner 1996, TIBS 21: 267-271, Table 1 (hereby incorporated by reference), for any one of the following proteins: GCN4, IκBα, Fos, Ornithine decarboxylase, Cactus, CLN2, CLN 3 or NIMA.

The modified Neurotoxin polypeptide encoded by the polynucleotide of the present invention will exhibit a reduced duration of the biological effect in a subject upon administration in comparison to an unmodified Neurotoxin polypeptide. In an aspect, the said biological effect observed in the subject causes muscle paralysis, i.e. a (reversible) inactivation of the muscle's capability to contract. In an aspect, the effects can be tested by the so-called mouse running assay (Keller 2006, Neuroscience 139: 629-637). The biological effects can be determined by the person skilled in the art without further ado. A is reduced duration of the biological effect, in an aspect, refers to a statistically significant reduced duration. Whether the duration of an effect is statistically significant reduced can be determined by those skilled in the art by applying standard statistical tests, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population. In an aspect, the said reduced duration persist less than 75%, less than 70%, less than 65%, less than 60%, less than 55%, less than 50%, less than 45%, less than 40%, less than 30% or less than 20% of the normal duration, i.e. the duration observed for an unmodified Neurotoxin polypeptide. In an aspect, normal duration persists for approximately 4 month in the case of BoNT/A, 2 months in the case of BoNT/B, approximately 3 to 4 months in the case of BoNT/C or approximately 4 weeks in the case of BoNT/E (Foran, J. Biol. Chem. 278(2): 1363-1371, Eleopra 1998, Neurosci Lett. 13, 256(3): 135-138, Eleopra 1997, Neurosci Lett. 14, 224(2): 91-94, Sloop 1997, Neurology 49(1): 189-194, Washbourne 1998, J Physiol Paris 92(2): 135-139). It is to be understood that the duration of the effect depends on individual influences in a subject such as genetic background, age, life style etc. Therefore, an approximate duration as meant herein refers to a duration as indicated above for the respective Neurotoxin polypeptides (e.g., 4 months for BoNT/A or 4 weeks for BoNT/E) with a standard deviation of 25% or less, 20% or less, 15% or less, 10% or less or 5% or less.

Advantageously, it has been found in accordance with the present invention that a Neurotoxin polypeptide can be modified to exhibit a shortened biological effect in a subject upon administration. In principle, this can be achieved by introducing or linking a degradation signal to the light chain of the said Neurotoxin polypeptide since it was found that the persistence of the light chain correlates with the duration of the biological effect. The shortened duration of the biological effect elicited by Neurotoxin polypeptides is beneficial for various medical applications which require an inactivation of nervous actions, e.g., muscle paralysis in order to facilitate wound healing.

The present invention contemplates a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, in an aspect, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Moreover, the present invention pertains to a host cell comprising the polynucleotide or the vector of the present invention.

The term "host cell" as used herein encompasses prokaryotic and eukaryotic host cells. In an aspect the host cell is a bacterial cell and, in another aspect, a Firmicutes bacterial cell. In one aspect, the said bacterial host cell is an *E. coli* host cell. In another aspect, it is a *Clostridium* host cell. In a further aspect, the said *Clostridium* host cell is a *Clostridium botulinum* host cell, in even a further aspect, a cell of one of the aforementioned seven different serotypes of *Clostridium botulinum*. In yet another aspect, the bacterial host cell is a *Clostridium tetani* host cell. In a further aspect, the host cell is a *Bacillus* host cell and in a particular aspect a *Bacillus megaterium* host cell. A eukaryotic host cell, in an aspect, is a cell of an animal cell line suitable for production of toxic proteins or a fungal host cell such as a yeast host cell.

Also encompassed by the present invention is a polypeptide encoded by the polynucleotide of the invention.

The term "polypeptide" as used herein encompasses isolated or essentially purified polypeptides being essentially free of other polypeptides including the complexing proteins (HA70, HA17, HA33, or NTNH (NBP) of the host cell or polypeptide preparations comprising other proteins in addition. Moreover, the term includes chemically modified polypeptides. Such modifications may be artificial modifications or naturally occurring modifications. As referred to above, the polypeptide of the present invention shall have the biological properties of the Neurotoxin polypeptides referred to above. Moreover, it shall exhibit shortened duration of the biological effect in a subject upon administration. The polypeptide of the invention, in an aspect, can be manufactured by a method of manufacturing a polypeptide as described elsewhere herein in more detail. In an aspect of the invention, a polypeptide preparation is also envisaged which comprises a complex of the Neurotoxin polypeptide and its complexing proteins.

Moreover, the present invention relates to an antibody which specifically binds to the polypeptide of the present invention.

Antibodies against the polypeptide of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. In an aspect, the antibody of the present invention is a monoclonal antibody, a polyclonal antibody, a single chain antibody, a human or humanized antibody or primatized, chimerized or fragment thereof. Also comprised as antibodies by the present invention is a bispecific antibody, a synthetic antibody, an antibody fragment, such as a Fab, Fv or scFv fragment etc., or a chemically modified derivative of any of these. The antibody of the present invention shall specifically bind (i.e. does not cross react with other polypeptides or peptides) to the polypeptide of the invention. Specifically, the antibody shall also not cross react with the unmodified Neurotoxin polypeptide. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described bei Köhler et al. (Köhler 1975, Nature 256 (1975), 495) or Galfré. (Galfré 1981, Meth. Enzymol. 73 (1981)) which comprise the fusion of mouse myeloma cells to spleen cells derived from mammals which have been immunized by the antigen, i.e. the polypeptide of the invention or a immunogenic fragment thereof. The antibodies can be used, for example, for the immunoprecipitation and immunolocalization of the polypeptides of the invention as well as for the monitoring of the presence of said polypeptides, for example, in recombinant organisms, and for the identification of compounds interacting with the proteins according to the invention. For example, surface plasmon resonance as employed in the BIAcore system can be used to increase the efficiency of phage antibodies which bind to an epitope of the protein of the invention (Schier 1996, Human Antibodies Hybridomas 7, 97-105; Malmborg 1995, J. Immunol. Methods 183, 7-13).

The polynucleotide or polypeptide of the invention can be used as a medicament, in general.

The term "medicament" as used herein refers, in one aspect, to a pharmaceutical composition containing the biologically active Neurotoxin polypeptide or a polynucleotide encoding it as pharmaceutical active compound. The said medicament may be used for human or animal therapy of various diseases or disorders in a therapeutically effective dose. The medicament can be formulated by various techniques dependent on the desired application purposes. Different aspects of a medicament according to the present invention are specified herein below.

In an aspect, the medicament comprises the biologically active Neurotoxin polypeptide of the present invention one or more pharmaceutically acceptable carrier as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pa. It will be understood that a carrier might also be a virus or retrovirus suitable for gene therapy, in particular, if the active ingredient of the medicament is the polynucleotide of the invention.

The medicament, in an aspect, will be dissolved in a diluent prior to administration. The diluent is also selected so as not to affect the biological activity of the combination. Examples of such diluents are distilled water or physiological saline. In addition, the pharmaceutical composition or formulation may also include other carriers or non-toxic, non-therapeutic, non-immunogenic stabilizers and the like. Thus, the Neurotoxin polypeptide of the invention can be present, in an aspect, in liquid or lyophilized form. In an aspect, it can be present together with glycerol, protein stabilizers (HSA) or non-protein stabilizers such as polyviylpyrolidon (PVP), hyaluronic acid or free amino acids. In an aspect, suitable non-proteinaceous stabilizers are disclosed in WO 2005/007185 or WO 2006/020208.

In another aspect, the medicament will be provided as a solution comprising the Neurotoxin polypeptide. Moreover, the solution can comprise carriers or stabilizers referred to above as well. A stable liquid formulation of the Neurotoxin polypeptide can be provided, in an aspect, as disclosed by U.S. Pat. No. 7,211,261.

The pharmaceutical composition is, in one aspect, administered topically. Conventionally the medicament will be administered intra-muscular or subcutaneous (near glands) depending on the desired medical indication. However, depending on the nature and the mode of action of a compound the pharmaceutical composition may be administered by other routes as well.

A therapeutically effective dose refers to an amount of the Neurotoxin polypeptide or the polynucleotide of the invention which prevents, ameliorates or treats the symptoms accompanying a condition or disease referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The medicament of the present invention will comprise, in an aspect, dosage recommendations in the prescribers or users instructions in order to anticipate dosage adjustments depending on the individual recipient.

The medicament referred to herein are developed to be administered at least once in order to treat or ameliorate or prevent a disease or condition recited in this specification. However, the said medicament may be administered more than one time.

The medicament according to the present invention may in a further aspect of the invention comprise drugs in addition to the biologically active Neurotoxin polypeptide which are added to the pharmaceutical composition during its formulation.

Moreover, the present invention pertains to the use of the polynucleotide or the polypeptide of the present invention for the preparation of a medicament for the treatment of wound healing, immobilization for bone and tendon fracture treatment, post surgery immobilization, specifically in connection with haemorrhoidectomy, introduction of dental implants, or hip joint replacement (endoprothesis), knee arthroplasty, ophthalmological surgery, acne, or irritable bowel disease.

The symptoms associated with the aforementioned medical conditions or diseases are well known to the person skilled in the art and are described in standard text books of medicine such as Stedman or Pschyrembl.

Moreover, the present invention also relates to the use of the polynucleotide or the polypeptide of the present invention for the preparation of a diagnostic medicament for determining whether a subject is susceptible for a Neurotoxin therapy.

The diagnostic medicament referred to above is a Neurotoxin polypeptide medicament as referred to above. However, the medicament is to be applied for a time and at a dosage regimen allowing merely the determination of whether a subject responds to the Neurotoxin polypeptide at all or the determination of a suitable dosage regimen. Since the above Neurotoxin polypeptide—although having therapeutic potential as well—is pivotally used for a diagnostic purpose rather than for treating or amelioration in this aspect, the medicament comprising it is termed "diagnostic medicament". Thus, such a time-restricted pre-screen with the modified Neurotoxin polypeptides of the present invention will assist in selecting subjects susceptible for a therapy using an unmodified Neurotoxin as well as in determining a suitable dosage. Potential side effects of a therapy based on an unmodified Neurotoxin which would normally persist over a longer time can be reduced due to the reduced duration of the biological effect elicited by the modified Neurotoxin polypeptide of the invention.

The present invention encompasses a method for the manufacture of a Neurotoxin polypeptide encoded by the polynucleotide of the invention comprising the steps of:
a) cultivating the host cell of the invention under conditions which allow for the expression of the Neurotoxin polypeptide encoded by the polynucleotide of the invention, and
b) obtaining the Neurotoxin polypeptide encoded by the polynucleotide of the invention from the host cell culture of a).

The polypeptide may be obtained from the culture, in an aspect, by all conventional purification techniques including affinity chromatography, size exclusion chromatography, high pressure liquid chromatography (HPLC) and precipitation techniques including antibody precipitation. Moreover, in an aspect the Neurotoxin polypeptide obtained by the method of the invention may be free of complexing proteins. In another aspect, the Neurotoxin polypeptide may be obtained as a complex comprising in addition to the Neurotoxin polypeptide complexing proteins. Moreover, obtaining as used herein, in an aspect, includes activation of the Neurotoxin polypeptide. This can be achieved by proteolytic cleavage of the (single-chain) Neurotoxin polypeptide precursor either intracellular by an endogenous or exogenous (e.g., recombinant expressed) protease or outside the cell by contacting the Neurotoxin polypeptide, e.g., prior, during or after the aforementioned purification, with the protease under conditions allowing for cleavage.

Furthermore, a method for the manufacture of a medicament is contemplated in accordance with the present invention, said method comprising the steps of the aforementioned method of the invention and the further step of formulating the Neurotoxin polypeptide encoded by the polynucleotide of the invention as a medicament.

It will be understood that such a method for the manufacture of a medicament is carried out according to the GMP standards for medicaments in order to ensure quality, pharmaceutical safety, and efficacy of the medicament. Suitable formulations of the medicament are described elsewhere in this specification. The person skilled in the art is, however, well aware of how such formulations can be made.

The invention also encompasses a method for the manufacture of a cosmetic composition comprising the steps of the method of the invention and the further step of formulating the Neurotoxin polypeptide as a cosmetic composition.

"Cosmetic composition" as used herein can be formulated as described for a pharmaceutical composition above. For a cosmetic composition, likewise, it is envisaged that the compound of the present invention is in an aspect used in substantially pure form. Impurities, however, may be less critical than for a medicament. Cosmetic compositions are, in a further aspect, to be applied intramuscular. In an even further aspect of the invention, cosmetic compositions comprising the Neurotoxin can be formulated as an anti-wrinkle agent.

The present invention also pertains to such a cosmetic composition and to the use of the polynucleotide or the polypeptide of the present invention for the preparation of a cosmetic composition to be used as an anti-wrinkle agent.

All references cited in this specification are herewith incorporated by reference with respect to their entire disclosure content and the disclosure content specifically mentioned in this specification.

The invention claimed is:

1. A modified polynucleotide encoding a *Clostridium botulinum* neurotoxin (BoNT) polypeptide exhibiting a reduced duration of a biological effect in a subject, wherein the neurotoxin polypeptide comprises at least one degradation signal in a light chain of the neurotoxin polypeptide, wherein the degradation signal in the light chain of the neurotoxin polypeptide is selected from:
 a) at least one internally or terminally introduced PEST motif;
 b) at least one internally or terminally introduced E3 ligase recognition motif.

2. The modified polynucleotide of claim 1, wherein the biological effect causes muscle paralysis in the subject.

3. The modified polynucleotide of claim 1, wherein the duration of the biological effect in a subject persists less than 4, 3 or 2 weeks.

4. The polynucleotide modified of claim 1, wherein the neurotoxin polypeptide is encoded by a sequence selected from:
 a) a nucleic acid sequence set forth as SEQ ID NO: 1, 3, 5, 7, 9, 11, or 13;
 b) a nucleic acid sequence encoding a polypeptide having an amino acid sequence as set forth as SEQ ID NO: 2, 4, 6, 8, 10, 12, or 14.

5. A vector comprising the polynucleotide of claim 1.

6. A host cell comprising the polynucleotide of claim 1.

7. The host cell of claim 6, wherein the host cell is selected from an *E. coli* cell, a *Clostridium* cell and a *Bacillus* cell.

8. A host cell comprising the vector of claim 5.

9. The host cell of claim 8, wherein the host cell is selected from an *E. coli* cell, a *Clostridium* cell and a *Bacillus* cell.

10. A method for the manufacture of a neurotoxin polypeptide exhibiting a reduced duration of a biological effect in a subject comprising the steps of:
   a) cultivating the host cell of claim 6 under conditions which allow for the expression of the neurotoxin polypeptide, and
   b) obtaining the neurotoxin polypeptide from the cultivated host cell of step a).

11. The method of claim 10, further comprising a step of formulating the neurotoxin polypeptide as a medicament comprising one or more pharmaceutically acceptable carriers.

* * * * *

UNITED STATES PATENT AND TRADEMARK OFFICE
CERTIFICATE OF CORRECTION

| | | |
|---|---|---|
| PATENT NO. | : 8,586,329 B2 | |
| APPLICATION NO. | : 13/381533 | |
| DATED | : November 19, 2013 | |
| INVENTOR(S) | : Fred Hofmann and Jurgen Frevert | |

It is certified that error appears in the above-identified patent and that said Letters Patent is hereby corrected as shown below:

Title Page, References Cited, Other Publication, line 21: "Jost, Drugs, vol. 57" should be --Jost, Drugs, vol. 67--.

Signed and Sealed this
Twenty-fifth Day of February, 2014

Michelle K. Lee
*Deputy Director of the United States Patent and Trademark Office*

SEQUENCE LISTING

<160> NUMBER OF SEQ ID NOS: 34

<210> SEQ ID NO 1
<211> LENGTH: 3891
<212> TYPE: DNA
<213> ORGANISM: Clostridium botulinum

<400> SEQUENCE: 1

```
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttggggtgga     360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
ggctctactc aatacattag atttagccca gattttacat ttggttttga ggagtcactt     600
```

```
gaagttgata caaatcctct tttaggtgca ggcaaatttg ctacagatcc agcagtaaca    660
ttagcacatg aacttataca tgctggacat agattatatg gaatagcaat taatccaaat    720
agggttttta agtaaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact taataaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaatttta ctaaactaaa aaattttact   1260
ggattgtttg aattttataa gttgctatgt gtaagaggga taataacttc taaaactaaa   1320
tcattagata aaggatacaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata cattttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaactta attggtcaag tagatagatt aaaagataaa   2520
gttaataata cacttagtac agatataccct tttcagcttt ccaaatacgt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa aacaaagagt agttttaaa   3000
```

-continued

```
tacagtcaaa tgattaatat atcagattat ataaacagat ggattttttgt aactatcact    3060 aataatagat taaataactc taaaatttat ataaatggaa gattaataga tcaaaaacca    3120
atttcaaatt taggtaatat tcatgctagt aataatataa tgtttaaatt agatggttgt    3180
agagatacac atagatatat ttggataaaa tattttaatc tttttgataa ggaattaaat    3240 gaaaagaaa tcaaagattt atatgataat caatcaaatt caggtattttt aaaagactttt   3300 tggggtgatt atttacaata tgataaacca tactatatgt taaatttata tgatccaaat   3360
aaatatgtcg atgtaaataa tgtaggtatt agaggttata tgtatcttaa agggcctaga    3420
ggtagcgtaa tgactacaaa catttattta aattcaagtt tgtatagggg gacaaaattt    3480
attataaaaa aatatgcttc tggaaataaa gataatattg ttagaaataa tgatcgtgta    3540
tatattaatg tagtagttaa aaataaagaa tataggttag ctactaatgc atcacaggca    3600
ggcgtagaaa aaatactaag tgcattagaa atacctgatg taggaaatct aagtcaagta    3660
gtagtaatga agtcaaaaaa tgatcaagga ataacaaata aatgcaaaat gaatttacaa    3720
gataataatg ggaatgatat aggctttata ggatttcatc agtttaataa tatagctaaa    3780
ctagtagcaa gtaattggta taatagacaa atagaaagat ctagtaggac tttgggttgc    3840
tcatgggaat ttattcctgt agatgatgga tggggagaaa ggccactgta a             3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220
```

-continued

```
Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
        260                 265                 270

Phe Ile Asp Ser Leu Gln Glu Asn Glu Phe Arg Leu Tyr Tyr Tyr Asn
    275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
    515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Ala Met Phe Leu Gly Trp Val Glu
    595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala Leu
625                 630                 635                 640

Leu Asn Ile Gly Asn Met Leu Tyr Lys Asp Asp Phe Val Gly Ala Leu
```

-continued

```
                645                 650                 655
Ile Phe Ser Gly Ala Val Ile Leu Leu Glu Phe Ile Pro Glu Ile Ala
                660                 665                 670
Ile Pro Val Leu Gly Thr Phe Ala Leu Val Ser Tyr Ile Ala Asn Lys
                675                 680                 685
Val Leu Thr Val Gln Thr Ile Asp Asn Ala Leu Ser Lys Arg Asn Glu
                690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
                755                 760                 765
Leu Ser Ser Lys Leu Asn Glu Ser Ile Asn Lys Ala Met Ile Asn Ile
                770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
                820                 825                 830
Gln Val Asp Arg Leu Lys Asp Lys Val Asn Asn Thr Leu Ser Thr Asp
                835                 840                 845
Ile Pro Phe Gln Leu Ser Lys Tyr Val Asp Asn Gln Arg Leu Leu Ser
                850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
                900                 905                 910
Gln Ile Gln Leu Phe Asn Leu Glu Ser Ser Lys Ile Glu Val Ile Leu
                915                 920                 925
Lys Asn Ala Ile Val Tyr Asn Ser Met Tyr Glu Asn Phe Ser Thr Ser
                930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
                980                 985                 990
Ile Lys Gln Arg Val Val Phe Lys Tyr Ser Gln Met Ile Asn Ile Ser
                995                 1000                1005
Asp Tyr Ile Asn Arg Trp Ile Phe Val Thr Ile Thr Asn Asn Arg
                1010                1015                1020
Leu Asn Asn Ser Lys Ile Tyr Ile Asn Gly Arg Leu Ile Asp Gln
                1025                1030                1035
Lys Pro Ile Ser Asn Leu Gly Asn Ile His Ala Ser Asn Asn Ile
                1040                1045                1050
Met Phe Lys Leu Asp Gly Cys Arg Asp Thr His Arg Tyr Ile Trp
                1055                1060                1065
```

| | | | | | | | | | | |
|---|---|---|---|---|---|---|---|---|---|---|
| Ile | Lys | Tyr | Phe | Asn | Leu | Phe | Asp | Lys | Glu | Leu | Asn | Glu | Lys | Glu |
| | 1070 | | | | 1075 | | | | 1080 | |

| Ile | Lys | Asp | Leu | Tyr | Asp | Asn | Gln | Ser | Asn | Ser | Gly | Ile | Leu | Lys |
| | 1085 | | | | 1090 | | | | 1095 | |

| Asp | Phe | Trp | Gly | Asp | Tyr | Leu | Gln | Tyr | Asp | Lys | Pro | Tyr | Tyr | Met |
| | 1100 | | | | 1105 | | | | 1110 | |

| Leu | Asn | Leu | Tyr | Asp | Pro | Asn | Lys | Tyr | Val | Asp | Val | Asn | Asn | Val |
| | 1115 | | | | 1120 | | | | 1125 | |

| Gly | Ile | Arg | Gly | Tyr | Met | Tyr | Leu | Lys | Gly | Pro | Arg | Gly | Ser | Val |
| | 1130 | | | | 1135 | | | | 1140 | |

| Met | Thr | Thr | Asn | Ile | Tyr | Leu | Asn | Ser | Ser | Leu | Tyr | Arg | Gly | Thr |
| | 1145 | | | | 1150 | | | | 1155 | |

| Lys | Phe | Ile | Ile | Lys | Lys | Tyr | Ala | Ser | Gly | Asn | Lys | Asp | Asn | Ile |
| | 1160 | | | | 1165 | | | | 1170 | |

| Val | Arg | Asn | Asn | Asp | Arg | Val | Tyr | Ile | Asn | Val | Val | Val | Lys | Asn |
| | 1175 | | | | 1180 | | | | 1185 | |

| Lys | Glu | Tyr | Arg | Leu | Ala | Thr | Asn | Ala | Ser | Gln | Ala | Gly | Val | Glu |
| | 1190 | | | | 1195 | | | | 1200 | |

| Lys | Ile | Leu | Ser | Ala | Leu | Glu | Ile | Pro | Asp | Val | Gly | Asn | Leu | Ser |
| | 1205 | | | | 1210 | | | | 1215 | |

| Gln | Val | Val | Met | Lys | Ser | Lys | Asn | Asp | Gln | Gly | Ile | Thr | Asn |
| | 1220 | | | | 1225 | | | | 1230 | |

| Lys | Cys | Lys | Met | Asn | Leu | Gln | Asp | Asn | Asn | Gly | Asn | Asp | Ile | Gly |
| | 1235 | | | | 1240 | | | | 1245 | |

| Phe | Ile | Gly | Phe | His | Gln | Phe | Asn | Asn | Ile | Ala | Lys | Leu | Val | Ala |
| | 1250 | | | | 1255 | | | | 1260 | |

| Ser | Asn | Trp | Tyr | Asn | Arg | Gln | Ile | Glu | Arg | Ser | Ser | Arg | Thr | Leu |
| | 1265 | | | | 1270 | | | | 1275 | |

| Gly | Cys | Ser | Trp | Glu | Phe | Ile | Pro | Val | Asp | Asp | Gly | Trp | Gly | Glu |
| | 1280 | | | | 1285 | | | | 1290 | |

| Arg | Pro | Leu |
| | 1295 | |

```
<210> SEQ ID NO 3
<211> LENGTH: 3876
<212> TYPE: DNA
<213> ORGANISM: Clostridium botulinum

<400> SEQUENCE: 3
```

| | | |
|---|---|---|
| atgccagtta caataaataa ttttaattat aatgatccta tgataaataa taatattatt | 60 |
| atgatggagc ctccatttgc gagaggtacg gggagatatt ataaagcttt taaaatcaca | 120 |
| gatcgtattt ggataatacc ggaaagatat acttttggat ataaacctga ggattttaat | 180 |
| aaaagttccg gtattttaa tagagatgtt tgtgaatatt atgatccaga ttacttaaat | 240 |
| actaatgata aaagaatat attttacaa acaatgatca agttattaa tagaatcaaa | 300 |
| tcaaaaccat tgggtgaaaa gttattagag atgattataa atggtatacc ttatcttgga | 360 |
| gatagacgtg ttccactcga agagtttaac acaaacattg ctagtgtaac tgttaataaa | 420 |
| ttaatcagta atccaggaga agtggagcga aaaaaggta ttttcgcaaa tttaataata | 480 |
| tttgacctg ggccagtttt aaatgaaat gagactatag ataggtat acaaaatcat | 540 |
| tttgcatcaa gggaaggctt cggggtata atgcaaatga gttttgccc agaatatgta | 600 |
| agcgtatta taatgttca agaaaacaaa ggcgcaagta tatttaatag acgtggatat | 660 |
| ttttcagatc cagccttgat attaatgcat gaacttatac atgttttaca tggattatat | 720 |

```
ggcattaaag tagatgattt accaattgta ccaaatgaaa aaaattttt tatgcaatct    780 acagatgcta tacaggcaga agaactatat acatttggag gacaagatcc cagcatcata   840
actccttcta cggataaaag tatctatgat aaagttttgc aaaattttag agggatagtt   900
gatagactta acaaggtttt agtttgcata tcagatccta acattaatat taatatatat  960
aaaaataaat ttaaagataa atataaattc gttgaagatt ctgagggaaa atatagtata  1020
gatgtagaaa gttttgataa attatataaa agcttaatgt ttggttttac agaaactaat  1080
atagcagaaa attataaaat aaaaactaga gcttcttatt ttagtgattc cttaccacca  1140
gtaaaaataa aaaatttatt agataatgaa atctatacta tagaggaagg gtttaatata  1200
tctgataaag atatggaaaa agaatataga ggtcagaata aagctataaa taaacaagct  1260
tatgaagaaa ttagcaagga gcatttggct gtatataaga tacaaatgtg taaaagtgtt  1320
aaagctccag gaatatgtat tgatgttgat aatgaagatt tgttctttat agctgataaa  1380
aatagttttt cagatgattt atctaaaaac gaaagaatag aatataatac acagagtaat  1440
tatatagaaa atgacttccc tataaatgaa ttaattttag atactgattt aataagtaaa  1500
atagaattac caagtgaaaa tacagaatca cttactgatt ttaatgtaga tgttccagta  1560
tatgaaaaac aacccgctat aaaaaaaatt tttacagatg aaaataccat ctttcaatat  1620
ttatactctc agacatttcc tctagatata agagatataa gtttaacatc ttcatttgat  1680
gatgcattat tattttctaa caaagtttat tcatttttt ctatggatta tattaaaact  1740
gctaataaag tggtagaagc aggattattt gcaggttggg tgaaacagat agtaaatgat  1800
tttgtaatcg aagctaataa aagcaatact atggataaaa ttgcagatat atctctaatt  1860
gttccttata taggattagc tttaaatgta ggaaatgaaa cagctaaagg aaattttgaa  1920
aatgcttttg agattgcagg agccagtatt ctactagaat ttataccaga acttttaata  1980
cctgtagttg gagccttttt attagaatca tatattgaca ataaaaataa aattattaaa  2040
acaatagata atgctttaac taaaagaaat gaaaaatgga gtgatatgta cggattaata  2100
gtagcgcaat ggctctcaac agttaatact caatttttata caataaaaga gggaatgtat  2160
aaggctttaa attatcaagc acaagcattg gaagaaataa taaaatacag atataatata  2220
tattctgaaa aagaaaagtc aaatattaac atcgatttta atgatataaa ttctaaactt  2280
aatgagggta ttaaccaagc tatagataat ataaataatt ttataaatgg atgttctgta  2340
tcatatttaa tgaaaaaaat gattccatta gctgtagaaa aattactaga ctttgataat  2400
actctcaaaa aaaatttgtt aaattatata gatgaaaata aattatattt gattggaagt  2460
gcagaatatg aaaaatcaaa agtaaataaa tacttgaaaa ccattatgcc gtttgatctt  2520
tcaatatata ccaatgatac aatactaata gaaatgttta ataaatataa tagcgaaatt  2580
ttaaataata ttatcttaaa tttaagatat aaggataata atttaataga tttatcagga  2640
tatggggcaa aggtagaggt tatatgatgga gtcgagctta atgataaaaa tcaatttaaa  2700
ttaactagtt cagcaaatag taagattaga gtgactcaaa atcagaatat catatttaat  2760
agtgtgttcc ttgattttag cgttagcttt tggataagaa tacctaaata taagaatgat  2820
ggtatacaaa attatattca taatgaatat acaataatta attgtatgaa aaataattcg  2880
ggctggaaaa tatctattag gggtaatagg ataaatatgga cttaattga tataaatgga  2940 aaaaccaaat cggtattttt tgaatataac ataagagaag atatatcaga gtatataaat  3000
agatggtttt ttgtaactat tactaataat ttgaataacg ctaaaatta tattaatggt  3060 aagctagaat caaatacaga tattaaagat ataagagaag ttattgctaa tggtgaaata  3120
```

-continued

```
atatttaaat tagatggtga tatagataga acacaattta tttggatgaa atatttcagt     3180 attttaata  cggaattaag tcaatcaaat attgaagaaa gatataaaat tcaatcatat    3240
agcgaatatt taaaagattt tgggaaat  cctttaatgt acaataaaga atattatatg     3300
tttaatgcgg ggaataaaaa ttcatatatt aaactaaaga aagattcacc tgtaggtgaa    3360
attttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctagat tttttaatt  taaatcaaga gtggagagta    3540
tatacctata aatattttaa gaagaggaa  gaaaaattgt ttttagctcc tataagtgat    3600
tctgatgagt tttacaatac tatacaaata aaagaatatg atgaacagcc aacatatagt    3660
tgtcagttgc tttttaaaaa agatgaagaa agtactgatg agataggatt gattggtatt    3720
catcgtttct acgaatctgg aattgtattt gaagagtata agattatttt ttgtataagt    3780
aaatggtact taaagagagt aaaaaggaaa ccatataatt taaaattggg atgtaattgg    3840
cagtttattc ctaaagatga agggtggact gaataa                              3876
```

<210> SEQ ID NO 4
<211> LENGTH: 1291
<212> TYPE: PRT
<213> ORGANISM: Clostridium botulinum

<400> SEQUENCE: 4

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
```

-continued

```
                245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
            275                 280                 285
Tyr Asp Lys Val Leu Gln Asn Phe Arg Gly Ile Val Asp Arg Leu Asn
            290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
            325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
            355                 360                 365
Thr Arg Ala Ser Tyr Phe Ser Asp Ser Leu Pro Pro Val Lys Ile Lys
            370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
            405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys Ala Pro Gly Ile Cys Ile Asp
            435                 440                 445
Val Asp Asn Glu Asp Leu Phe Phe Ile Ala Asp Lys Asn Ser Phe Ser
            450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
            485                 490                 495
Leu Ile Ser Lys Ile Glu Leu Pro Ser Glu Asn Thr Glu Ser Leu Thr
            500                 505                 510
Asp Phe Asn Val Asp Val Pro Val Tyr Glu Lys Gln Pro Ala Ile Lys
            515                 520                 525
Lys Ile Phe Thr Asp Glu Asn Thr Ile Phe Gln Tyr Leu Tyr Ser Gln
            530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Ser Met Asp
            565                 570                 575
Tyr Ile Lys Thr Ala Asn Lys Val Val Glu Ala Gly Leu Phe Ala Gly
            580                 585                 590
Trp Val Lys Gln Ile Val Asn Asp Phe Val Ile Glu Ala Asn Lys Ser
            595                 600                 605
Asn Thr Met Asp Lys Ile Ala Asp Ile Ser Leu Ile Val Pro Tyr Ile
            610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
            645                 650                 655
Glu Leu Leu Ile Pro Val Val Gly Ala Phe Leu Leu Glu Ser Tyr Ile
            660                 665                 670
```

-continued

```
Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
                930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990

Glu Asp Ile Ser Glu Tyr Ile Asn Arg Trp Phe Phe Val Thr Ile Thr
                995                 1000                1005

Asn Asn Leu Asn Asn Ala Lys Ile Tyr Ile Asn Gly Lys Leu Glu
        1010                1015                1020

Ser Asn Thr Asp Ile Lys Asp Ile Arg Glu Val Ile Ala Asn Gly
        1025                1030                1035

Glu Ile Ile Phe Lys Leu Asp Gly Asp Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Arg Tyr Lys Ile Gln Ser Tyr Ser Glu Tyr
        1070                1075                1080

Leu Lys Asp Phe Trp Gly Asn Pro Leu Met Tyr Asn Lys Glu Tyr
        1085                1090                1095
```

| Tyr | Met | Phe | Asn | Ala | Gly | Asn | Lys | Asn | Ser | Tyr | Ile | Lys | Leu | Lys |
|-----|-----|-----|-----|-----|-----|-----|-----|-----|-----|-----|-----|-----|-----|-----|
| | 1100 | | | | 1105 | | | | 1110 | | | | | |

Lys Asp Ser Pro Val Gly Glu Ile Leu Thr Arg Ser Lys Tyr Asn
    1115                  1120                  1125

Gln Asn Ser Lys Tyr Ile Asn Tyr Arg Asp Leu Tyr Ile Gly Glu
    1130                  1135                  1140

Lys Phe Ile Ile Arg Arg Lys Ser Asn Ser Gln Ser Ile Asn Asp
    1145                  1150                  1155

Asp Ile Val Arg Lys Glu Asp Tyr Ile Tyr Leu Asp Phe Phe Asn
    1160                  1165                  1170

Leu Asn Gln Glu Trp Arg Val Tyr Thr Tyr Lys Tyr Phe Lys Lys
    1175                  1180                  1185

Glu Glu Glu Lys Leu Phe Leu Ala Pro Ile Ser Asp Ser Asp Glu
    1190                  1195                  1200

Phe Tyr Asn Thr Ile Gln Ile Lys Glu Tyr Asp Glu Gln Pro Thr
    1205                  1210                  1215

Tyr Ser Cys Gln Leu Leu Phe Lys Lys Asp Glu Glu Ser Thr Asp
    1220                  1225                  1230

Glu Ile Gly Leu Ile Gly Ile His Arg Phe Tyr Glu Ser Gly Ile
    1235                  1240                  1245

Val Phe Glu Glu Tyr Lys Asp Tyr Phe Cys Ile Ser Lys Trp Tyr
    1250                  1255                  1260

Leu Lys Glu Val Lys Arg Lys Pro Tyr Asn Leu Lys Leu Gly Cys
    1265                  1270                  1275

Asn Trp Gln Phe Ile Pro Lys Asp Glu Gly Trp Thr Glu
    1280                  1285                  1290

<210> SEQ ID NO 5
<211> LENGTH: 3843
<212> TYPE: DNA
<213> ORGANISM: Clostridium botulinum

<400> SEQUENCE: 5

| atgccaataa caattaacaa ctttaattat tcagatcctg ttgataataa aaatatttta | 60 |
|---|---|
| tatttagata ctcatttaaa tacattagct aatgagcctg aaaaagcctt tcgcattata | 120 |
| gggaatatat gggtaatacc cgatagattt tcaagagatt ctaatccaaa tttaaataaa | 180 |
| cctcctcgag ttacaagccc taaaagtggt tattatgatc ctaattattt gagtactgat | 240 |
| tctgaaaaag atacattttt aaaagaaatt ataaagttat ttaaaagaat taactctaga | 300 |
| gaaataggag aagaattaat atatagactt gcaacagaca tacccttttcc tgggaataac | 360 |
| aatactccaa ttaatacttt tgattttgat gtagatttta acagtgttga tgttaaaact | 420 |
| agacaaggta caactgggt taaaactggt agtataaatc ctagtgttat aataactgga | 480 |
| cctagagaaa acattataga cccagaaact tctacgttta aattaactaa caatactttt | 540 |
| gcggcacaag aaggatttgg tgctttatca ataatttcaa tatcacctag atttatgcta | 600 |
| acatatagta atgcaactaa taatgtagga gagggtagat tttctaagtc tgaattttgc | 660 |
| atggatccaa tactaatttt aatgcatgaa cttaatcatg caatgcataa tttatatgga | 720 |
| atagctatac caaatgatca agaatttca tctgtaacta gtaatatttt ttattctcaa | 780 |
| tataaggtga attagagta tgcagaaata tatgcatttg gaggtccaac tatagacctt | 840 |
| attcctaaaa gtgcaaggaa atattttgag gaaaaggcat ggattatta tagatccata | 900 |
| gctaaaagac ttaatagtat aactactgca aatcccttcaa gctttaataa atatatagga | 960 |

```
gaatataaac agaaacttat tagaaagtat agattcgtag tagaatcttc aggtgaagtt      1020
gcagtagatc gtaataagtt tgctgagtta tataaagaac ttacacaaat atttacagaa      1080
tttaactacg ctaaaatata taatgtacaa aataggaaaa tatatctttc aaatgtatat      1140
actccggtta cggcaaatat attagacgat aatgttatg atatacaaaa tggatttaac       1200
atacctaaaa gtaatttaaa tgtactattt atgggtcaaa atttatctcg aaatccagca      1260
ttaagaaaag tcaatcctga aaatatgctt tatttattta caaaattttg ccataaagca      1320
atagatggta gatcattata taataaaaca ttagattgta gagagctttt agttaaaaat      1380
actgacttac cctttatagg tgatattagt gatatcaaaa ctgatatatt tttaagcaaa      1440
gatattaatg aagaaactga agttatagac tatccggaca atgtttcagt ggatcaagtt      1500
attctcagta agaatacctc agaacatgga caactagatt tattataccc tattattgaa      1560
ggtgagagtc aagtattacc gggagagaat caagtctttt atgataatag aactcaaaat      1620
gttgattatt tgaattctta ttattaccta gaatctcaaa aactaagtga taatgttgaa      1680
gattttactt ttacgacatc aattgaggaa gctttggata atagtggaaa agtatatact      1740
tactttccta aactagctga taaagtaaat acgggtgttc aaggtggttt attttaatg       1800 tgggcaaatg atgtagttga agatttact acaaatattc taagaaaaga tacattagat       1860
aaaatatcag atgtatcagc tattattccc tatataggac ctgcattaaa tataagtaat      1920
tctgtaagaa ggggaaattt tactgaagca tttgcagtta ccggtgtaac tatttattaa      1980
gaagcgtttc aagaatttac aatacctgca cttggtgcat ttgtgattta tagtaaggtt      2040
caagaaagaa acgagattat taaaactata gataattgtt tagaacaaag gattaaaaga      2100
tggaaagatt catatgaatg gatgatagga acgtggttat ccaggattac tactcaattt      2160
aataatataa gttatcaaat gtatgattct ttaaattatc aggcagatgc aatcaaagat      2220
aaaatagatt tagaatataa aaaatactca ggaagtgata agaaaaatat aaaaagtcaa      2280
gttgaaaatt taaaaaatag tttagatata aaaatctcgg aagcaatgaa taatataaat      2340
aaatttatac gagaatgttc tgtaacatac ttatttaaaa atatgctccc taaagtaatt      2400
gatgaattaa ataagtttga tttaaaaact aaaacagaat taattaatct tatagatagt      2460
cataatatta ttctagttgg tgaagtagat agattaaaag caaagtaaa tgagagtttt       2520 gaaaatacaa taccctttaa tatttttca tatactaata attctttatt aaagatata       2580 attaatgaat atttcaatag tattaatgat tcaaaatttt tgagcttaca aaacaaaaaa      2640
aatgctttag tggatacatc aggatataat gcagaagtga ggctagaagg tgatgttcaa      2700
gttaatacga tatatacaaa tgattttaaa ttaagtagtt caggagataa aattatagta      2760
aatttaaata ataatatttt atatagcgct atttatgaga actctagtgt tagttttgg       2820 attaagatat ctaaagattt aactaattct cataatgaat atacaataat taatagtata      2880
aaacaaaatt ctgggtggaa attatgtatt aggaatggca atatagaatg gattttacaa      2940
gatattaata gaaagtataa agtttaatt tttgattata gtgaatcatt aagtcataca       3000
ggatatacaa ataatggtt ttttgttact ataactaata atataatggg gtatatgaaa       3060
ctttatataa atggagaatt aaagcagagt gaaagaattg aagatttaaa tgaggttaag      3120
ttagataaaa ccatagtatt tggaatagat gagaatatag atgagaatca gatgctttgg      3180
attagagatt ttaatatttt ttctaaagaa ttaagcaatg aagatattaa tattgtatat      3240
gagggacaaa tattaagaaa tgttattaaa gattattggg gaaatccttt gaagtttgat      3300
acagaatatt atattattaa tgataattat atagataggt atatagcacc taaaagtaat      3360
```

-continued

```
atacttgtac ttgttcagta tccagataga tctaaattat atactggaaa tcctattact    3420
attaaatcag tatctgataa gaatccttat agtagaattt taaatggaga taatataatg    3480
tttcatatgt tatataatag tgggaaatat atgataataa gagatactga tacaatatat    3540
gcaatagaag gaagagagtg ttcaaaaaat tgtgtatatg cattaaaatt acagagtaat    3600
ttaggtaatt atggtatagg tatatttagt ataaaaaata ttgtatctca aaataaatat    3660
tgtagtcaaa ttttctctag ttttatgaaa aatacaatgc ttctagcaga tatatataaa    3720
ccttggagat tttcttttga aaatgcatac acgccagttg cagtaactaa ttatgagaca    3780
aaactattat caacttcatc ttttttggaaa tttatttcta gggatccagg atgggtagag    3840
taa                                                                    3843
```

<210> SEQ ID NO 6
<211> LENGTH: 1280
<212> TYPE: PRT
<213> ORGANISM: Clostridium botulinum

<400> SEQUENCE: 6

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285
```

-continued

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Ile Gly Thr Trp Leu Ser Arg Ile Thr Thr Gln Phe
705                 710                 715                 720
```

```
Asn Asn Ile Ser Tyr Gln Met Tyr Asp Ser Leu Asn Tyr Gln Ala Asp
            725                 730                 735

Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Ile Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
            805                 810                 815

Leu Ile Asp Ser His Asn Ile Ile Leu Val Gly Glu Val Asp Arg Leu
            820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
            850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
            885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Asn Ile Leu Tyr
            915                 920                 925

Ser Ala Ile Tyr Glu Asn Ser Ser Val Ser Phe Trp Ile Lys Ile Ser
            930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
            965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr Gly Tyr Thr Asn Lys Trp Phe Phe
            995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asn Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Ile Ile Asn Asp Asn Tyr Ile Asp Arg
    1100                1105                1110

Tyr Ile Ala Pro Lys Ser Asn Ile Leu Val Leu Val Gln Tyr Pro
    1115                1120                1125

Asp Arg Ser Lys Leu Tyr Thr Gly Asn Pro Ile Thr Ile Lys Ser
```

| | | | | | | | | | | |
|---|---|---|---|---|---|---|---|---|---|---|
| | | | 1130 | | | 1135 | | | 1140 | |
| Val | Ser | Asp | Lys | Asn | Pro | Tyr | Ser | Arg | Ile | Leu | Asn | Gly | Asp | Asn |
| 1145 | | | | | 1150 | | | | | 1155 |
| Ile | Met | Phe | His | Met | Leu | Tyr | Asn | Ser | Gly | Lys | Tyr | Met | Ile | Ile |
| 1160 | | | | | 1165 | | | | | 1170 |
| Arg | Asp | Thr | Asp | Thr | Ile | Tyr | Ala | Ile | Glu | Gly | Arg | Glu | Cys | Ser |
| 1175 | | | | | 1180 | | | | | 1185 |
| Lys | Asn | Cys | Val | Tyr | Ala | Leu | Lys | Leu | Gln | Ser | Asn | Leu | Gly | Asn |
| 1190 | | | | | 1195 | | | | | 1200 |
| Tyr | Gly | Ile | Gly | Ile | Phe | Ser | Ile | Lys | Asn | Ile | Val | Ser | Gln | Asn |
| 1205 | | | | | 1210 | | | | | 1215 |
| Lys | Tyr | Cys | Ser | Gln | Ile | Phe | Ser | Ser | Phe | Met | Lys | Asn | Thr | Met |
| 1220 | | | | | 1225 | | | | | 1230 |
| Leu | Leu | Ala | Asp | Ile | Tyr | Lys | Pro | Trp | Arg | Phe | Ser | Phe | Glu | Asn |
| 1235 | | | | | 1240 | | | | | 1245 |
| Ala | Tyr | Thr | Pro | Val | Ala | Val | Thr | Asn | Tyr | Glu | Thr | Lys | Leu | Leu |
| 1250 | | | | | 1255 | | | | | 1260 |
| Ser | Thr | Ser | Ser | Phe | Trp | Lys | Phe | Ile | Ser | Arg | Asp | Pro | Gly | Trp |
| 1265 | | | | | 1270 | | | | | 1275 |
| Val | Glu |
| 1280 |

<210> SEQ ID NO 7
<211> LENGTH: 3858
<212> TYPE: DNA
<213> ORGANISM: Clostridium botulinum

<400> SEQUENCE: 7

```
atgacatggc cagtaaaaga ttttaattat agtgatcctg ttaatgacaa tgatatatta      60
tatttaagaa taccacaaaa taagttaatt actacacctg taaaagcttt tatgattact     120
caaaatattt gggtaatacc agaaagattt tcatcagata ctaatccaag tttaagtaaa     180
ccgcctagac ctacttcaaa gtatcaaagt tattatgatc ctagttattt atctactgat     240
gagcaaaaag atacattttt aaaagggatt ataaaattat ttaaaagaat taatgaaaga     300
gatataggaa aaaaattaat aaattattta gtagttggtt caccttttat gggagattca     360
agtacgcctg aagatacatt tgattttaca cgtcatacta ctaatattgc agttgaaaag     420
tttgaaaatg gtagttggaa agtaacaaat attataacac aagtgtatt gatatttgga     480
ccacttccta atatattaga ctatacagca tcccttacat tgcaaggaca acaatcaaat     540
ccatcatttg aagggtttgg aacattatct atactaaaag tagcacctga attttttgtta    600
acatttagtg atgtaacatc taatcaaagt tcagctgtat taggcaaatc tatattttgt     660
atggatccag taatagcttt aatgcatgag ttaacacatt ctttgcatca attgtatgga     720
ataaatatac catctgataa aaggattcgt ccacaagtta gcgagggatt ttttctctcaa    780
gatggaccca acgtacaatt tgaggaatta tacacatttg gaggatcaga tgttgaaata     840
atacctcaaa ttgaaagatt acaattaaga gaaaaagcat taggtcacta taaagatata     900
gcgaaaagac ttaataatat taataaaact attccttcta gttggagtag taatatagat     960
aaatataaaa aaatattttc tgaaaagtat aattttgata agataaatac aggaaatttt    1020
gttgtaaata ttgataaatt caatagctta tattcagact tgactaatgt tatgtcagaa    1080
gttgtttatt cttcgcaata taatgttaaa acaggactca ttattttttc aaagcattat    1140
ctacctgtat ttgcaaatat attagatgat aatatttata ctataataaa cggttttaat    1200
```

```
ttaacaacta aaggttttaa tatagaaaat tcgggtcaga atatagaaag gaatcctgca      1260
ctacaaaaac ttagttcaga aagtgtagta gatttgttta caaaagtatg tttaagatta      1320
acaagaaata gtagagatga ttcaacatgt attcaagtta aaaataatac attaccttat      1380
gtagctgata aagatagcat ttcacaagaa atatttgaaa gtcaaattat tacagatgag      1440
actaatgtag aaaattattc agataatttt tcattagatg aatctatttt agatgcaaaa      1500
gtccctacta atcctgaagc agtagatcca ctgttaccca atgttaatat ggaacctttta     1560 aatgttccag gtgaagaaga agtattttat gatgatatta ctaaagatgt tgattattta     1620
aactcttatt attatttgga agcccaaaaa ttaagtaata atgttgaaaa tattactctt     1680
acaacttcag ttgaagaagc attaggttat agcaataaga tatacacatt tttacctagc     1740
ttagctgaaa aagtgaataa aggtgttcaa gcaggtttat tcttaaattg ggcgaatgaa     1800
gtagttgagg attttactac aaatattatg aaaaaagata cattggataa aatatcagat     1860
gtatcagcca taattccata tataggacct gccttaaata taggaaattc agcattaagg     1920
ggaaacttta agcaagcatt tgcaacagct ggtgtagctt ttttgttaga aggatttcca     1980
gagtttacaa tacctgcact cggtgtattt accttttata gttctattca agaaagagag     2040
aaaattatta aaactataga aaattgttta gaacaaagag ttaagagatg gaaagattca     2100
tatcaatgga tggtatcaaa ttggttgtca agaattacta ctcgatttaa tcatataagt     2160
tatcaaatgt atgattcttt gagttatcag gcagatgcaa tcaaagctaa aatagattta     2220
gaatataaaa aatactcagg aagtgataaa gaaaatataa aaagtcaagt tgaaaattta     2280
aaaaatagtt tagatgtaaa aatctcggaa gcaatgaata atataaataa atttatacga     2340
gaatgttctg taacatactt atttaaaaat atgctcccta aagtaattga tgaattaaat     2400
aagtttgatt taaaaactaa aacagaatta attaatctta tagatagtca taatattatt     2460
ctagttggtg aagtagatag attaaaagca aaagtaaatg agagttttga aaatacaata     2520 cccttttaata tttttttcata tactaataat tctttattaa agatatgat taatgaatat     2580 ttcaatagta ttaatgattc aaaaattttg agcttacaaa ataaaaaaaa tactttgatg     2640
gatacatcag gatataacgc agaagtgaga gtagaaggca atgttcagct taatccaata     2700
tttccatttg actttaaatt aggtagttca ggggatgata gaggtaaagt tatagtaacc     2760
cagaatgaaa atattgtata taatgctatg tatgaaagtt ttagtattag tttttggatt     2820
aggataaata aatgggtaag taatttacct ggatatacta taattgatag tgttaaaaat     2880
aactcaggtt ggagtatagg tattattagt aattttttag tgtttacttt aaaacaaaat     2940
gaaaatagtg aacaagatat aaactttagt tatgatatat caagaatgc tgcgggatat     3000 aataaatggt tttttgtaac tattactacc aatatgatgg gaaatatgat gatttatata     3060
aatggaaaat taatagatac tataaaagtt aaagagttaa ctggaattaa ttttagcaaa     3120
actataacat ttcaaatgaa taaaattcca aatactggct taattacctc agattctgat     3180
aacatcaata tgtggataag ggattttttat atctttgcta agaattaga tgataaagat     3240 attaatatat tatttaatag cttgcaatat actaatgttg taaagattaa ttggggaaat     3300
gatttaagat atgataaaga atattacatg attaacgtaa attatatgaa tagatatatg     3360
tctaaaaaag gcaatggaat tgtttttaat acacgtaaaa ataataatga cttcaatgaa     3420
ggatataaaa ttataataaa aagaattaga ggaaatacaa atgatactag agtacgagga     3480
gaaaatgtat tatattttaa tactacaatt gataacaaac aatatagttt aggtatgtat     3540
aaaccttcta gaaatctagg gactgattta gttccactag gtgcattgga tcaaccaatg     3600
```

-continued

```
gatgagatac gtaaatatgg ttcgtttata atacaaccat gcaatacttt tgattactat   3660
gcatcacaat tattttttgtc aagtaatgca acaacaaata ggcttggaat actatcaatt   3720
ggtagttata gtttcaaact tggagatgac tattggttta atcacgaata tttaattcct   3780
gttataaaaa tagagcatta tgcttcatta ttagaatcaa catcaactca ttgggttttt   3840
gtacctgcaa gtgaataa                                                 3858
```

<210> SEQ ID NO 8
<211> LENGTH: 1285
<212> TYPE: PRT
<213> ORGANISM: Clostridium botulinum

<400> SEQUENCE: 8

```
Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335
```

```
Thr Gly Asn Phe Val Val Asn Ile Asp Lys Phe Asn Ser Leu Tyr Ser
        340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Lys His Tyr Leu Pro Val Phe
    370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
                420                 425                 430

Phe Thr Lys Val Cys Leu Arg Leu Thr Arg Asn Ser Arg Asp Asp Ser
            435                 440                 445

Thr Cys Ile Gln Val Lys Asn Asn Thr Leu Pro Tyr Val Ala Asp Lys
    450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
                500                 505                 510

Pro Asn Val Asn Met Glu Pro Leu Asn Val Pro Gly Glu Glu Glu Val
            515                 520                 525

Phe Tyr Asp Asp Ile Thr Lys Asp Val Asp Tyr Leu Asn Ser Tyr Tyr
        530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Ala Ile
    610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Arg Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
```

-continued

```
            755                 760                 765
Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
                820                 825                 830

Asn Glu Ser Phe Glu Asn Thr Ile Pro Phe Asn Ile Phe Ser Tyr Thr
            835                 840                 845

Asn Asn Ser Leu Leu Lys Asp Met Ile Asn Glu Tyr Phe Asn Ser Ile
850                 855                 860

Asn Asp Ser Lys Ile Leu Ser Leu Gln Asn Lys Lys Asn Thr Leu Met
865                 870                 875                 880

Asp Thr Ser Gly Tyr Asn Ala Glu Val Arg Val Glu Gly Asn Val Gln
                885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
        915                 920                 925

Ala Met Tyr Glu Ser Phe Ser Ile Ser Phe Trp Ile Arg Ile Asn Lys
        930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
        995                 1000                1005

Thr Thr Asn Met Met Gly Asn Met Met Ile Tyr Ile Asn Gly Lys
    1010                1015                1020

Leu Ile Asp Thr Ile Lys Val Lys Glu Leu Thr Gly Ile Asn Phe
    1025                1030                1035

Ser Lys Thr Ile Thr Phe Gln Met Asn Lys Ile Pro Asn Thr Gly
    1040                1045                1050

Leu Ile Thr Ser Asp Ser Asp Asn Ile Asn Met Trp Ile Arg Asp
    1055                1060                1065

Phe Tyr Ile Phe Ala Lys Glu Leu Asp Asp Lys Asp Ile Asn Ile
    1070                1075                1080

Leu Phe Asn Ser Leu Gln Tyr Thr Asn Val Val Lys Asp Tyr Trp
    1085                1090                1095

Gly Asn Asp Leu Arg Tyr Asp Lys Glu Tyr Tyr Met Ile Asn Val
    1100                1105                1110

Asn Tyr Met Asn Arg Tyr Met Ser Lys Lys Gly Asn Gly Ile Val
    1115                1120                1125

Phe Asn Thr Arg Lys Asn Asn Asn Asp Phe Asn Glu Gly Tyr Lys
    1130                1135                1140

Ile Ile Ile Lys Arg Ile Arg Gly Asn Thr Asn Asp Thr Arg Val
    1145                1150                1155

Arg Gly Glu Asn Val Leu Tyr Phe Asn Thr Thr Ile Asp Asn Lys
    1160                1165                1170
```

| | | | | | | | | | | |
|---|---|---|---|---|---|---|---|---|---|---|
|Gln|Tyr|Ser|Leu|Gly|Met|Tyr|Lys|Pro|Ser|Arg|Asn|Leu|Gly|Thr|
| |1175| | | |1180| | | |1185| |

Asp Leu Val Pro Leu Gly Ala Leu Asp Gln Pro Met Asp Glu Ile
    1190            1195            1200

Arg Lys Tyr Gly Ser Phe Ile Ile Gln Pro Cys Asn Thr Phe Asp
    1205            1210            1215

Tyr Tyr Ala Ser Gln Leu Phe Leu Ser Ser Asn Ala Thr Thr Asn
    1220            1225            1230

Arg Leu Gly Ile Leu Ser Ile Gly Ser Tyr Ser Phe Lys Leu Gly
    1235            1240            1245

Asp Asp Tyr Trp Phe Asn His Glu Tyr Leu Ile Pro Val Ile Lys
    1250            1255            1260

Ile Glu His Tyr Ala Ser Leu Leu Glu Ser Thr Ser Thr His Trp
    1265            1270            1275

Val Phe Val Pro Ala Ser Glu
    1280            1285

<210> SEQ ID NO 9
<211> LENGTH: 3756
<212> TYPE: DNA
<213> ORGANISM: Clostridium botulinum

<400> SEQUENCE: 9

```
atgccaaaaa ttaatagttt taattataat gatcctgtta atgatagaac aatttttatat    60 attaaaccag gcggttgtca agaattttat aaatcattta atattatgaa aaatatttgg   120
ataattccag agagaaatgt aattggtaca acccccccaag attttcatcc gcctacttca   180
ttaaaaaatg gagatagtag ttattatgac cctaattatt tacaaagtga tgaagaaaag   240
gatagatttt taaaaatagt cacaaaaata tttaatagaa taataataa tctttcagga   300 gggatttat tagaagaact gtcaaaagct aatccatatt tagggaatga taatactcca   360
gataatcaat tccatattgg tgatgcatca gcagttgaga ttaaattctc aaatggtagc   420
caagacatac tattacctaa tgttattata atgggagcag agcctgattt atttgaaact   480
aacagttcca atatttctct aagaaataat tatatgccaa gcaatcaccg ttttggatca   540
atagctatag taacattctc acctgaatat tcttttagat ttaatgataa ttgtatgaat   600
gaatttattc aagatcctgc tcttacatta atgcatgaat aatacattc attacatgga   660 ctatatgggg ctaaagggat tactacaaag tatactataa cacaaaaaca aaatccccta   720
ataacaaata taagaggtac aaatattgaa gaattcttaa cttttggagg tactgattta   780
aacattatta ctagtgctca gtccaatgat atctatacta atcttctagc tgattataaa   840
aaaatagcgt ctaaacttag caaagtacaa gtatctaatc cactacttaa tccttataaa   900
gatgtttttg aagcaaagta tggattagat aaagatgcta gcggaattta ttcggtaaat   960
ataaacaaat ttaatgatat tttttaaaaa ttatacagct ttacggaatt tgatttacga  1020
actaaatttc aagttaaatg taggcaaact tatattggac agtataaata cttcaaactt  1080
tcaaacttgt taaatgattc tatttataat atatcagaag gctataatat aaataattta  1140
aaggtaaatt ttagaggaca gaatgcaaat ttaaatccta gaattattac accaattaca  1200
ggtagaggac tagtaaaaaa aatcattaga ttttgtaaaa atattgtttc tgtaaaaggc  1260
ataaggaaat caatatgtat cgaaataaat aatggtgagt tatttttgt ggcttccgag  1320 aatagttata atgatgataa tataaatact cctaaagaaa ttgacgatac agtaacttca  1380
aataataatt atgaaaatga tttagatcag gttatttaa attttaatag tgaatcagca  1440
```

```
cctggacttt cagatgaaaa attaaattta actatccaaa atgatgctta tataccaaaa    1500
tatgattcta atggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat tttttcatc agaatttatt    1680
aataatgtca ataaacctgt gcaagcagca ttatttgtaa gctggataca acaagtgtta    1740
gtagatttta ctactgaagc taaccaaaaa agtactgttg ataaaattgc agatatttct    1800
atagttgttc catatatagg tcttgcttta aatataggaa atgaagcaca aaaaggaaat    1860
tttaaagatg cacttgaatt attaggagca ggtatttat  tagaatttga acccgagctt    1920
ttaattccta caattttagt attcacgata aaatcttttt taggttcatc tgataataaa    1980
aataaagtta ttaaagcaat aaataatgca ttgaaagaaa gagatgaaaa atggaaagaa    2040
gtatatagtt ttatagtatc gaattggatg actaaaatta atacacaatt taataaaaga    2100
aaagaacaaa tgtatcaagc tttacaaaat caagtaaatg caattaaaac aataatagaa    2160
tctaagtata atagttatac tttagaggaa aaaaatgagc ttacaaataa atatgatatt    2220
aagcaaatag aaaatgaact taatcaaaag gtttctatag caatgaataa tatagacagg    2280
ttcttaactg aaagttctat atcctattta atgaaaataa taaatgaagt aaaaattaat    2340
aaattaagag aatatgatga gaatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaattttaat ttcatatttt    2520
aataaattct ttaagagaat taaaagtagt tcagttttaa atatgagata taaaaatgat    2580
aaatacgtag atacttcagg atatgattca aatataaaata ttaatggaga tgtatataaa    2640
tatccaacta ataaaaatca atttggaata tataatgata aacttagtga agttaatata    2700
tctcaaaatg attacattat atatgataat aaatataaaa attttagtat tagttttttgg   2760
gtaagaattc ctaactatga taataagata gtaaatgtta ataatgaata cactataata    2820
aattgtatga gagataataa ttcaggatgg aaagtatctc ttaatcataa tgaaataatt    2880
tggacattcg aagataatcg aggaattaat caaaaattag catttaacta tggtaacgca    2940
aatggtattt ctgattatat aaataagtgg atttttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatatttt  gataaagaat tagatgaaac agaaattcaa    3180
actttatata gcaatgaacc taatacaaat attttgaagg attttggggg aaattatttg    3240
ctttatgaca agaatactaa tttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttatttt   3480
ccattatatg ctgatacagc taccacaaat aaagagaaaa caataaaaat atcatcatct    3540
ggcaatagat ttaatcaagt agtagttatg aattcagtag gaaattgtac aatgaatttt    3600
aaaaataata atgaaataa tattgggttg ttaggtttca aggcagatac tgtcgttgct    3660
agtacttggt attatacaca tatgagagat catacaaaca gcaatggatg tttttggaac    3720
tttatttctg aagaacatgg atggcaagaa aaataa                              3756
```

<210> SEQ ID NO 10

-continued

<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Arg Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400
```

-continued

Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
                420                 425                 430
Glu Leu Phe Phe Val Ala Ser Glu Asn Ser Tyr Asn Asp Asp Asn Ile
                435                 440                 445
Asn Thr Pro Lys Glu Ile Asp Asp Thr Val Thr Ser Asn Asn Asn Tyr
                450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
                515                 520                 525
Pro Glu Gly Glu Asn Asn Val Asn Leu Thr Ser Ser Ile Asp Thr Ala
                530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
                580                 585                 590
Val Asp Lys Ile Ala Asp Ile Ser Ile Val Val Pro Tyr Ile Gly Leu
                595                 600                 605
Ala Leu Asn Ile Gly Asn Glu Ala Gln Lys Gly Asn Phe Lys Asp Ala
                610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
                675                 680                 685
Trp Met Thr Lys Ile Asn Thr Gln Phe Asn Lys Arg Lys Glu Gln Met
                690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
                755                 760                 765
Tyr Leu Met Lys Ile Ile Asn Glu Val Lys Ile Asn Lys Leu Arg Glu
                770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                805                 810                 815
Asp Thr Leu Asn Asn Ser Ile Pro Phe Lys Leu Ser Ser Tyr Thr Asp

```
                        820                 825                 830
Asp Lys Ile Leu Ile Ser Tyr Phe Asn Lys Phe Lys Arg Ile Lys
            835                 840                 845
Ser Ser Ser Val Leu Asn Met Arg Tyr Lys Asn Asp Lys Tyr Val Asp
            850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
            885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
                915                 920                 925
Lys Ile Val Asn Val Asn Asn Glu Tyr Thr Ile Ile Asn Cys Met Arg
            930                 935                 940
Asp Asn Asn Ser Gly Trp Lys Val Ser Leu Asn His Asn Glu Ile Ile
945                 950                 955                 960
Trp Thr Phe Glu Asp Asn Arg Gly Ile Asn Gln Lys Leu Ala Phe Asn
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu Gly Asp Ser Lys Leu Tyr Ile Asn
                995                 1000                1005
Gly Asn Leu Ile Asp Gln Lys Ser Ile Leu Asn Leu Gly Asn Ile
        1010                1015                1020
His Val Ser Asp Asn Ile Leu Phe Lys Ile Val Asn Cys Ser Tyr
        1025                1030                1035
Thr Arg Tyr Ile Gly Ile Arg Tyr Phe Asn Ile Phe Asp Lys Glu
        1040                1045                1050
Leu Asp Glu Thr Glu Ile Gln Thr Leu Tyr Ser Asn Glu Pro Asn
        1055                1060                1065
Thr Asn Ile Leu Lys Asp Phe Trp Gly Asn Tyr Leu Leu Tyr Asp
        1070                1075                1080
Lys Glu Tyr Tyr Leu Leu Asn Val Leu Lys Pro Asn Asn Phe Ile
        1085                1090                1095
Asp Arg Arg Lys Asp Ser Thr Leu Ser Ile Asn Asn Ile Arg Ser
        1100                1105                1110
Thr Ile Leu Leu Ala Asn Arg Leu Tyr Ser Gly Ile Lys Val Lys
        1115                1120                1125
Ile Gln Arg Val Asn Asn Ser Ser Thr Asn Asp Asn Leu Val Arg
        1130                1135                1140
Lys Asn Asp Gln Val Tyr Ile Asn Phe Val Ala Ser Lys Thr His
        1145                1150                1155
Leu Phe Pro Leu Tyr Ala Asp Thr Ala Thr Thr Asn Lys Glu Lys
        1160                1165                1170
Thr Ile Lys Ile Ser Ser Ser Gly Asn Arg Phe Asn Gln Val Val
        1175                1180                1185
Val Met Asn Ser Val Gly Asn Cys Thr Met Asn Phe Lys Asn Asn
        1190                1195                1200
Asn Gly Asn Asn Ile Gly Leu Leu Gly Phe Lys Ala Asp Thr Val
        1205                1210                1215
Val Ala Ser Thr Trp Tyr Tyr Thr His Met Arg Asp His Thr Asn
        1220                1225                1230
```

Ser Asn Gly Cys Phe Trp Asn Phe Ile Ser Glu Glu His Gly Trp
    1235                1240                1245

Gln Glu Lys
    1250

<210> SEQ ID NO 11
<211> LENGTH: 3843
<212> TYPE: DNA
<213> ORGANISM: Clostridium botulinum

<400> SEQUENCE: 11

```
atgccagttg taataaatag ttttaattat aatgaccctg ttaatgatga gacaatttta      60
tacatgcaga aaccatatga agaaagaagt agaaaatatt ataaagcttt tgagattatg     120
cctaatgttt ggataatgcc tgagagagat acaataggaa ctaagcctga tgagtttcag     180
gtgccggatt cattaaagaa cggaagtagt gcttattatg atcctaatta tttaaccact     240
gatgctgaaa aagatagata tttaaaaaca atgataaaat tatttaatag aattaatagt     300
aatcctacag ggaaagtttt gttagaagaa gtatcaaatg ctagaccata tttaggagat     360
gatgacacgc taattaatga attccttcca gttaatgtaa ctacaagtgt aatatataaa     420
ttttcaactg atgttgaaag ttcaataata tcgaatcttc ttgtattggg agcaggacct     480
gatatattta agcttactg tacccccctt gtaaggttta ataagtcaga taaattaatt     540
gaaccaagta atcatggttt tggatcaatt aatatcttga cattttcacc tgagtatgaa     600
catatttta atgatattag tggagggaat cataatagta cagaatcatt tattgcagat     660
cctgcaattt cactagctca tgaattgata catgcactac atggattata cggggctaag     720
gcagttactc ataaagagtc tctagtagca gagcgaggac ctcttatgat agccgaaaag     780
cccataaggc tagaagaatt tttaactttt ggaggtgagg atttaaatat cattcctagt     840
gctatgaagg aaaaaatata taacgatctt ttagctaact atgaaaaaat agctactaga     900
cttagagaag ttaatacggc tcctcctgga tatgatatta tgaatataa agattatttt     960
caatggaagt atggactaga tagaaatgca gatggaagtt atactgtgaa tagaaataaa    1020
tttaatgaaa tttataaaaa attatatagc tttacagaga ttgacttagc aaataaattt    1080
aaagtaaaat gtagaaatac ttattttatt aaatatggat ttgtaaaagt tccaaatttg    1140
ttagatgatg atatttatac tgtatcagag gggtttaata taggtaattt agcagtaaac    1200
aatcgcggac aaaatataaa tttaaatcct aaaattattg attccattcc agataaaggt    1260
ttagtggaaa agattattaa attttgtaag agcattattc ctagaaaagg tacgaagcag    1320
tcaccgtcac tatgcattag agtaaataat agggagttat tttttgtagc ttcagaaagt    1380
agctataatg aaagtgatat taatacacct aaagaaattg acgatacaac aaatctaaat    1440
aataattata gaaataattt agatgaagtt attttagatt ataatagtga gacaatacct    1500
caaatatcaa atcgaacatt aaatacactt gtacaagaca atagttatgt gccaagatat    1560
gattctaatg aacaagtgaa atagaggaa tatgatgttg ttgacttaa tgtatttttc    1620
tatttacatg cacaaaaagt accagaaggt gaaaccaata taagtttaac ttcttcaatt    1680
gatacagcat tattagaaga atccaaagta tatacatttt tttcttcaga gtttatcgat    1740
actatcaata aacctgtaaa tgcagcacta tttatagatt ggataagcaa agtaataaga    1800
gatttttacca ctgaagctac acaaaaaagt actgttgata agattgcaga catatcttta    1860
attgtacccct atgtaggtct tgctttgaat atagttattg aggcagaaaa aggaaatttt    1920
gaggaggcat ttgaattatt aggagcgggt atttttatta aatttgtgcc agagcttaca    1980
```

```
attcctgtaa ttttagtgtt tacgataaaa tcctatatag attcatatga gaataaaaat    2040
aaagcaatta aagcaataaa taattcatta atcgaaagag aagcaaagtg aaagaaata     2100 tatagttgga tagtatcaaa ttggcttact agaattaata cgcaatttaa taaagaaaa     2160 gagcaaatgt atcaggcttt acaaaatcaa gtagatgcaa taaaaacagc aatagaatat    2220
aaatataata attatacttc agatgagaaa aatagacttg aatctaaata taatatcaat    2280
aatatagaag aagaattgaa taaaaaagtt tctttagcaa tgaaaaatat agaaagattt    2340
atgacagaaa gttctatatc ttatttaatg aaattaataa atgaagccga gttggtaaa    2400 ttaaaagaat atgataaaca tgttaagagc gatttattag actatattct ctaccataaa    2460
ttaatcttag gagagcagac aaaggaatta attgatttgg tgactagtac tttgaatagt    2520
agtattccat ttgaactttc ttcatatact aatgataaaa ttctaattat atattttaat    2580
agattatata aaaaaattaa agatagttct attttagata tgcgatatga aataataaaa    2640
tttatagata tctctggata tggttcaaat ataagcatta atggaaacgt atatattat    2700 tcaacaaata gaaatcaatt tggaatatat agtggtaggc ttagtgaagt taatatagct    2760
caaaataatg atattatata caatagtaga tatcaaaatt ttagtattag tttctgggta    2820
accattccta aacactacag acctatgaat cgtaatcggg aatacactat aataaattgt    2880
atggggaata taattcggg atggaaaata tcacttagaa ctattagaga ttgtgaaata    2940
atttggactt tacaagatac ttccggaaat aaggaaaaat taattttag gtatgaagaa    3000 cttgctagta tatctgatta tataaataaa tggatttttg taactattac taataataga    3060
ttaggcaatt ctagaattta catcaatgga aatttaatag ttgaaaaatc aatttcgaat    3120
ttaggtgata ttcatgttag tgataatata ttatttaaaa ttgttggttg tgatgatgaa    3180
acgtatgttg gtataagata tttttaaagtt tttaatacgg aattagataa aacagaaatt    3240
gagactttat atagtaatga gccagatcca agtatcttaa aagactattg gggaaattat    3300
ttgctatata taaaaaaata ttatttattc aatttactaa gaaaagataa gtatattact    3360
cggaattcag gcatttaaa tattaatcaa caaagaggtg ttactggagg catatctgtt    3420
tttttgaact ataaattata tgaaggagta gaagttatta taagaaaaaa tgctcctata    3480
gatatatcta atacgataa ttttgttaga aaaacgatc tagcatacat taatgtagta    3540
gatcatggtg tagaatatcg gttatatgct gatatatcaa ttcaaaaatc agagaaaata    3600
ataaaattaa taagaacatc taatccaaac gatagcttag gtcaaattat agttatggat    3660
tcaataggaa ataattgcac aatgaatttt caaaacaatg atgggagcaa tataggatta    3720
ctaggttttc attcagatga tttggttgct agtagttggt attataacca tatacgaaga    3780
aacactagca gtaatggatg cttttggagt tttatttcta aagagcatgg ttggaaagaa    3840
taa                                                                 3843
```

<210> SEQ ID NO 12
<211> LENGTH: 1280
<212> TYPE: PRT
<213> ORGANISM: Clostridium botulinum

<400> SEQUENCE: 12

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

```
Arg Asp Thr Ile Gly Thr Lys Pro Asp Glu Phe Gln Val Pro Asp Ser
     50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Met Ile Lys Leu Phe Asn
                 85                  90                  95

Arg Ile Asn Ser Asn Pro Thr Gly Lys Val Leu Leu Glu Glu Val Ser
                100                 105                 110

Asn Ala Arg Pro Tyr Leu Gly Asp Asp Thr Leu Ile Asn Glu Phe
            115                 120                 125

Leu Pro Val Asn Val Thr Thr Ser Val Asn Ile Lys Phe Ser Thr Asp
        130                 135                 140

Val Glu Ser Ser Ile Ile Ser Asn Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
        435                 440                 445

Asn Asn Arg Glu Leu Phe Phe Val Ala Ser Glu Ser Ser Tyr Asn Glu
450                 455                 460

Ser Asp Ile Asn Thr Pro Lys Glu Ile Asp Asp Thr Thr Asn Leu Asn
```

-continued

```
            465                 470                 475                 480
Asn Asn Tyr Arg Asn Asn Leu Asp Glu Val Ile Leu Asp Tyr Asn Ser
                    485                 490                 495
Glu Thr Ile Pro Gln Ile Ser Asn Arg Thr Leu Asn Thr Leu Val Gln
                    500                 505                 510
Asp Asn Ser Tyr Val Pro Arg Tyr Asp Ser Asn Gly Thr Ser Glu Ile
                    515                 520                 525
Glu Glu Tyr Asp Val Val Asp Phe Asn Val Phe Phe Tyr Leu His Ala
                    530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Val Tyr Thr Phe Phe Ser Ser
                    565                 570                 575
Glu Phe Ile Asp Thr Ile Asn Lys Pro Val Asn Ala Ala Leu Phe Ile
                    580                 585                 590
Asp Trp Ile Ser Lys Val Ile Arg Asp Phe Thr Thr Glu Ala Thr Gln
                    595                 600                 605
Lys Ser Thr Val Asp Lys Ile Ala Asp Ile Ser Leu Ile Val Pro Tyr
                    610                 615                 620
Val Gly Leu Ala Leu Asn Ile Val Ile Glu Ala Glu Lys Gly Asn Phe
625                 630                 635                 640
Glu Glu Ala Phe Glu Leu Leu Gly Ala Gly Ile Leu Leu Glu Phe Val
                    645                 650                 655
Pro Glu Leu Thr Ile Pro Val Ile Leu Val Phe Thr Ile Lys Ser Tyr
                    660                 665                 670
Ile Asp Ser Tyr Glu Asn Lys Asn Lys Ala Ile Lys Ala Ile Asn Asn
                    675                 680                 685
Ser Leu Ile Glu Arg Glu Ala Lys Trp Lys Glu Ile Tyr Ser Trp Ile
                    690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Ala Ile Lys Thr
                    725                 730                 735
Ala Ile Glu Tyr Lys Tyr Asn Asn Tyr Thr Ser Asp Glu Lys Asn Arg
                    740                 745                 750
Leu Glu Ser Lys Tyr Asn Ile Asn Asn Ile Glu Glu Leu Asn Lys
                    755                 760                 765
Lys Val Ser Leu Ala Met Lys Asn Ile Glu Arg Phe Met Thr Glu Ser
770                 775                 780
Ser Ile Ser Tyr Leu Met Lys Leu Ile Asn Glu Ala Glu Val Gly Lys
785                 790                 795                 800
Leu Lys Glu Tyr Asp Lys His Val Lys Ser Asp Leu Leu Asp Tyr Ile
                    805                 810                 815
Leu Tyr His Lys Leu Ile Leu Gly Glu Gln Thr Lys Glu Leu Ile Asp
                    820                 825                 830
Leu Val Thr Ser Thr Leu Asn Ser Ser Ile Pro Phe Glu Leu Ser Ser
                    835                 840                 845
Tyr Thr Asn Asp Lys Ile Leu Ile Ile Tyr Phe Asn Arg Leu Tyr Lys
                    850                 855                 860
Lys Ile Lys Asp Ser Ser Ile Leu Asp Met Arg Tyr Glu Asn Asn Lys
865                 870                 875                 880
Phe Ile Asp Ile Ser Gly Tyr Gly Ser Asn Ile Ser Ile Asn Gly Asn
                    885                 890                 895
```

-continued

```
Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Tyr Asn
        915                 920                 925

Ser Arg Tyr Gln Asn Phe Ser Ile Ser Phe Trp Val Thr Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
            980                 985                 990

Lys Leu Ile Phe Arg Tyr Glu Glu  Leu Ala Ser Ile Ser  Asp Tyr Ile
        995                 1000                1005

Asn Lys  Trp Ile Phe Val Thr  Ile Thr Asn Asn Arg  Leu Gly Asn
    1010                1015                1020

Ser Arg  Ile Tyr Ile Asn Gly  Asn Leu Ile Val Glu  Lys Ser Ile
    1025                1030                1035

Ser Asn  Leu Gly Asp Ile His  Val Ser Asp Asn Ile  Leu Phe Lys
    1040                1045                1050

Ile Val  Gly Cys Asp Asp Glu  Thr Tyr Val Gly Ile  Arg Tyr Phe
    1055                1060                1065

Lys Val  Phe Asn Thr Glu Leu  Asp Lys Thr Glu Ile  Glu Thr Leu
    1070                1075                1080

Tyr Ser  Asn Glu Pro Asp Pro  Ser Ile Leu Lys Asp  Tyr Trp Gly
    1085                1090                1095

Asn Tyr  Leu Leu Tyr Asn Lys  Lys Tyr Tyr Leu Phe  Asn Leu Leu
    1100                1105                1110

Arg Lys  Asp Lys Tyr Ile Thr  Arg Asn Ser Gly Ile  Leu Asn Ile
    1115                1120                1125

Asn Gln  Gln Arg Gly Val Thr  Gly Gly Ile Ser Val  Phe Leu Asn
    1130                1135                1140

Tyr Lys  Leu Tyr Glu Gly Val  Glu Val Ile Ile Arg  Lys Asn Ala
    1145                1150                1155

Pro Ile  Asp Ile Ser Asn Thr  Asp Asn Phe Val Arg  Lys Asn Asp
    1160                1165                1170

Leu Ala  Tyr Ile Asn Val Val  Asp His Gly Val Glu  Tyr Arg Leu
    1175                1180                1185

Tyr Ala  Asp Ile Ser Ile Thr  Lys Ser Glu Lys Ile  Ile Lys Leu
    1190                1195                1200

Ile Arg  Thr Ser Asn Pro Asn  Asp Ser Leu Gly Gln  Ile Ile Val
    1205                1210                1215

Met Asp  Ser Ile Gly Asn Asn  Cys Thr Met Asn Phe  Gln Asn Asn
    1220                1225                1230

Asp Gly  Ser Asn Ile Gly Leu  Leu Gly Phe His Ser  Asp Asp Leu
    1235                1240                1245

Val Ala  Ser Ser Trp Tyr Tyr  Asn His Ile Arg Arg  Asn Thr Ser
    1250                1255                1260

Ser Asn  Gly Cys Phe Trp Ser  Phe Ile Ser Lys Glu  His Gly Trp
    1265                1270                1275

Lys Glu
    1280

<210> SEQ ID NO 13
```

```
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13
```

| | | | | | |
|---|---|---|---|---|---|
| atgccagtta | atataaaaan | ctttaattat | aatgaccccta | ttaataatga | tgacattatt | 60 |
| atgatggaac | cattcaatga | cccagggcca | ggaacatatt | ataaagcttt | taggattata | 120 |
| gatcgtattt | ggatagtacc | agaaaggttt | acttatggat | ttcaacctga | ccaatttaat | 180 |
| gccagtacag | gagttttttag | taaagatgtc | tacgaatatt | acgatccaac | ttatttaaaa | 240 |
| accgatgctg | aaaaagataa | attttttaaaa | acaatgatta | aattatttaa | tagaattaat | 300 |
| tcaaaaccat | caggacagag | attactggat | atgatagtag | atgctatacc | ttatcttgga | 360 |
| aatgcatcta | caccgcccga | caaatttgca | gcaaatgttg | caaatgtatc | tattaataaa | 420 |
| aaaattatcc | aacctggagc | tgaagatcaa | ataaaaggtt | taatgacaaa | tttaataata | 480 |
| tttggaccag | gaccagttct | aagtgataat | tttactgata | gtatgattat | gaatggccat | 540 |
| tccccaatat | cagaaggatt | tggtgcaaga | atgatgataa | gattttgtcc | tagttgttta | 600 |
| aatgtattta | ataatgttca | ggaaaataaa | gatacatcta | tatttagtag | acgcgcgtat | 660 |
| tttgcagatc | cagctctaac | gttaatgcat | gaacttatac | atgtgttaca | tggattatat | 720 |
| ggaattaaga | taagtaattt | accaattact | ccaaatacaa | aagaattttt | catgcaacat | 780 |
| agcgatcctg | tacaagcaga | agaactatat | acattcggag | gacatgatcc | tagtgttata | 840 |
| agtccttcta | cggatatgaa | atatttataat | aaagcgttac | aaaattttca | agatatagct | 900 |
| aataggctta | atattgtttc | aagtgcccaa | gggagtggaa | ttgatatttc | cttatataaa | 960 |
| caaatatata | aaaataaata | tgattttgtt | gaagatccta | atggaaaata | tagtgtagat | 1020 |
| aaggataagt | ttgataaatt | atataaggcc | ttaatgtttg | gctttactga | aactaatcta | 1080 |
| gctggtgaat | atggaataaa | aactaggtat | tcttattttta | gtgaatattt | gccaccgata | 1140 |
| aaaactgaaa | aattgttaga | caatacaatt | tatactcaaa | atgaaggctt | taacatagct | 1200 |
| agtaaaaatc | tcaaaacgga | atttaatggt | cagaataagg | cggtaaataa | agaggcttat | 1260 |
| gaagaaatca | gcctagaaca | tctcgttata | tatagaaatg | caatgtgcaa | gcctgtaatg | 1320 |
| tacaaaaata | ccggtaaatc | tgaacagtgt | attattgtta | ataatgagga | tttattttc | 1380 |
| atagctaata | aagatagttt | ttcaaaagat | ttagctaaag | cagaaactat | agcatataat | 1440 |
| acacaaaata | atactataga | aaataatttt | tctatagatc | agttgatttt | agataatgat | 1500 |
| ttaagcagtg | gcatagactt | accaaatgaa | acacagaac | catttacaaa | ttttgacgac | 1560 |
| atagatatcc | ctgtgtatat | taaacaatct | gctttaaaaaa | aaatttttgt | ggatggagat | 1620 |
| agcctttttg | aatatttaca | tgctcaaaca | tttccttcta | atatagaaaa | tctacaacta | 1680 |
| acgaattcat | taaatgatgc | tttaagaaat | aataataaag | tctatacttt | tttttctaca | 1740 |
| aaccttgttg | aaaagctaa | tacagttgta | ggtgcttcac | ttttttgtaaa | ctgggtaaaa | 1800 |
| ggagtaatag | atgattttac | atctgaatcc | acacaaaaaa | gtactataga | taaagtttca | 1860 |
| gatgtatcca | taattattcc | ctatatagga | cctgctttga | atgtaggaaa | tgaaacagct | 1920 |
| aaagaaaatt | ttaaaaatgc | ttttgaaata | ggtggagccg | ctatcttaat | ggagtttatt | 1980 |
| ccagaactta | ttgtacctat | agttggattt | tttacattag | aatcatatgt | aggaaataaa | 2040 |
| gggcatatta | ttatgacgat | atccaatgct | ttaaagaaaa | gggatcaaaa | atggacagat | 2100 |

-continued

```
atgtatggtt tgatagtatc gcagtggctc tcaacggtta atactcaatt ttatacaata    2160
aaagaaagaa tgtacaatgc tttaaataat caatcacaag caatagaaaa ataatagaa     2220
gatcaatata atagatatag tgaagaagat aaaatgaata ttaacattga ttttaatgat    2280
atagatttta aacttaatca agtataaat ttagcaataa acaatataga tgattttata     2340
aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaagtaa atagacacct aaaagacagt    2520
ataccatttg atctttcact atataccaag gacacaattt taatcaagt ttttaataat    2580
tatattagta atattagtag taatgctatt ttaagtttaa gttatagagg tgggcgttta   2640
atagattcat ctggatatgg tgcaactatg aatgtaggtt cagatgttat ctttaatgat   2700
ataggaaatg gtcaatttaa attaaataat tctgaaaata gtaatattac ggcacatcaa   2760
agtaaattcg ttgtatatga tagtatgttt gataatttta gcattaactt ttgggtaagg   2820
actcctaaat ataataataa tgatatacaa acttatcttc aaaatgagta tacaataatt   2880
agttgtataa aaaatgactc aggatggaaa gtatctatta agggaaatag aataatatgg   2940
acattaatag atgttaatgc aaaatctaaa tcaatatttt tcgaatatag tataaaagat   3000
aatatatcag attatataaa taatggttt tccataacta ttactaatga tagattaggt    3060
aacgcaaata tttatataaa tggaagtttg aaaaaaagtg aaaaaatttt aaacttagat   3120
agaattaatt ctagtaatga tatagacttc aaattaatta attgtacaga tactactaaa   3180
tttgtttgga ttaaggattt taatattttt ggtagagaat aaatgctac agaagtatct    3240
tcactatatt ggattcaatc atctacaaat acttaaaag attttgggg gaatcctta     3300
agatacgata cacaatacta tctgtttaat caaggtatgc aaaatatcta tataaagtat   3360
tttagtaaag cttctatggg ggaaactgca ccacgtacaa actttaataa tgcagcaata   3420
aattatcaaa atttatatct tggtttacga tttattataa aaaaagcatc aaattctcgg   3480
aatataaata atgataatat agtcagagaa ggagattata tatatcttaa tattgataat   3540
atttctgatg aatcttacag agtatatgtt ttggtgaatt ctaaagaaat tcaaactcaa   3600
ttattttag cacccataaa tgatgatcct acgttctatg atgtactaca ataaaaaaa     3660
tattatgaaa aaacaacata taattgtcag atactttgcg aaaaagatac taaaacattt   3720
gggctgtttg gaattggtaa atttgttaaa gattatggat atgtttggga tacctatgat   3780
aattattttt gcataagtca gtggtatctc agaagaaat ctgaaaatat aaataaatta    3840
aggttgggat gtaattggca attcattccc gtggatgaag gatggacaga taa          3894
```

<210> SEQ ID NO 14
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 14

Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

-continued

```
Arg Phe Thr Tyr Gly Phe Gln Pro Asp Gln Phe Asn Ala Ser Thr Gly
 50                  55                  60

Val Phe Ser Lys Asp Val Tyr Glu Tyr Tyr Asp Pro Thr Tyr Leu Lys
 65                      70                  75                  80

Thr Asp Ala Glu Lys Asp Lys Phe Leu Lys Thr Met Ile Lys Leu Phe
                     85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
                115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
                180                 185                 190

Ile Arg Phe Cys Pro Ser Cys Leu Asn Val Phe Asn Asn Val Gln Glu
                195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
                275                 280                 285

Tyr Asn Lys Ala Leu Gln Asn Phe Gln Asp Ile Ala Asn Arg Leu Asn
                290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
                355                 360                 365

Arg Tyr Ser Tyr Phe Ser Glu Tyr Leu Pro Pro Ile Lys Thr Glu Lys
                370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
                450                 455                 460

Asp Ser Phe Ser Lys Asp Leu Ala Lys Ala Glu Thr Ile Ala Tyr Asn
```

```
                465                 470                 475                 480
    Thr Gln Asn Asn Thr Ile Glu Asn Asn Phe Ser Ile Asp Gln Leu Ile
                        485                 490                 495
    Leu Asp Asn Asp Leu Ser Ser Gly Ile Asp Leu Pro Asn Glu Asn Thr
                        500                 505                 510
    Glu Pro Phe Thr Asn Phe Asp Asp Ile Asp Ile Pro Val Tyr Ile Lys
                        515                 520                 525
    Gln Ser Ala Leu Lys Lys Ile Phe Val Asp Gly Asp Ser Leu Phe Glu
                        530                 535                 540
    Tyr Leu His Ala Gln Thr Phe Pro Ser Asn Ile Glu Asn Leu Gln Leu
    545                 550                 555                 560
    Thr Asn Ser Leu Asn Asp Ala Leu Arg Asn Asn Lys Val Tyr Thr
                        565                 570                 575
    Phe Phe Ser Thr Asn Leu Val Glu Lys Ala Asn Thr Val Val Gly Ala
                        580                 585                 590
    Ser Leu Phe Val Asn Trp Val Lys Gly Val Ile Asp Asp Phe Thr Ser
                        595                 600                 605
    Glu Ser Thr Gln Lys Ser Thr Ile Asp Lys Val Ser Asp Val Ser Ile
                        610                 615                 620
    Ile Ile Pro Tyr Ile Gly Pro Ala Leu Asn Val Gly Asn Glu Thr Ala
    625                 630                 635                 640
    Lys Glu Asn Phe Lys Asn Ala Phe Glu Ile Gly Gly Ala Ala Ile Leu
                        645                 650                 655
    Met Glu Phe Ile Pro Glu Leu Ile Val Pro Ile Val Gly Phe Phe Thr
                        660                 665                 670
    Leu Glu Ser Tyr Val Gly Asn Lys Gly His Ile Ile Met Thr Ile Ser
                        675                 680                 685
    Asn Ala Leu Lys Lys Arg Asp Gln Lys Trp Thr Asp Met Tyr Gly Leu
                        690                 695                 700
    Ile Val Ser Gln Trp Leu Ser Thr Val Asn Thr Gln Phe Tyr Thr Ile
    705                 710                 715                 720
    Lys Glu Arg Met Tyr Asn Ala Leu Asn Asn Gln Ser Gln Ala Ile Glu
                        725                 730                 735
    Lys Ile Ile Glu Asp Gln Tyr Asn Arg Tyr Ser Glu Glu Asp Lys Met
                        740                 745                 750
    Asn Ile Asn Ile Asp Phe Asn Asp Ile Asp Phe Lys Leu Asn Gln Ser
                        755                 760                 765
    Ile Asn Leu Ala Ile Asn Asn Ile Asp Asp Phe Ile Asn Gln Cys Ser
                        770                 775                 780
    Ile Ser Tyr Leu Met Asn Arg Met Ile Pro Leu Ala Val Lys Lys Leu
    785                 790                 795                 800
    Lys Asp Phe Asp Asp Asn Leu Lys Arg Asp Leu Leu Glu Tyr Ile Asp
                        805                 810                 815
    Thr Asn Glu Leu Tyr Leu Leu Asp Glu Val Asn Ile Leu Lys Ser Lys
                        820                 825                 830
    Val Asn Arg His Leu Lys Asp Ser Ile Pro Phe Asp Leu Ser Leu Tyr
                        835                 840                 845
    Thr Lys Asp Thr Ile Leu Ile Gln Val Phe Asn Asn Tyr Ile Ser Asn
                        850                 855                 860
    Ile Ser Ser Asn Ala Ile Leu Ser Leu Ser Tyr Arg Gly Gly Arg Leu
    865                 870                 875                 880
    Ile Asp Ser Ser Gly Tyr Gly Ala Thr Met Asn Val Gly Ser Asp Val
                        885                 890                 895
```

```
Ile Phe Asn Asp Ile Gly Asn Gly Gln Phe Lys Leu Asn Asn Ser Glu
                900                 905                 910
Asn Ser Asn Ile Thr Ala His Gln Ser Lys Phe Val Tyr Asp Ser
            915                 920                 925
Met Phe Asp Asn Phe Ser Ile Asn Phe Trp Val Arg Thr Pro Lys Tyr
    930                 935                 940
Asn Asn Asn Asp Ile Gln Thr Tyr Leu Gln Asn Glu Tyr Thr Ile Ile
945                 950                 955                 960
Ser Cys Ile Lys Asn Asp Ser Gly Trp Lys Val Ser Ile Lys Gly Asn
                965                 970                 975
Arg Ile Ile Trp Thr Leu Ile Asp Val Asn Ala Lys Ser Lys Ser Ile
            980                 985                 990
Phe Phe Glu Tyr Ser Ile Lys Asp Asn Ile Ser Asp Tyr Ile Asn Lys
        995                 1000                1005
Trp Phe Ser Ile Thr Ile Thr Asn Asp Arg Leu Gly Asn Ala Asn
    1010                1015                1020
Ile Tyr Ile Asn Gly Ser Leu Lys Lys Ser Glu Lys Ile Leu Asn
    1025                1030                1035
Leu Asp Arg Ile Asn Ser Ser Asn Asp Ile Asp Phe Lys Leu Ile
    1040                1045                1050
Asn Cys Thr Asp Thr Thr Lys Phe Val Trp Ile Lys Asp Phe Asn
    1055                1060                1065
Ile Phe Gly Arg Glu Leu Asn Ala Thr Glu Val Ser Ser Leu Tyr
    1070                1075                1080
Trp Ile Gln Ser Ser Thr Asn Thr Leu Lys Asp Phe Trp Gly Asn
    1085                1090                1095
Pro Leu Arg Tyr Asp Thr Gln Tyr Tyr Leu Phe Asn Gln Gly Met
    1100                1105                1110
Gln Asn Ile Tyr Ile Lys Tyr Phe Ser Lys Ala Ser Met Gly Glu
    1115                1120                1125
Thr Ala Pro Arg Thr Asn Phe Asn Asn Ala Ala Ile Asn Tyr Gln
    1130                1135                1140
Asn Leu Tyr Leu Gly Leu Arg Phe Ile Ile Lys Lys Ala Ser Asn
    1145                1150                1155
Ser Arg Asn Ile Asn Asn Asp Asn Ile Val Arg Glu Gly Asp Tyr
    1160                1165                1170
Ile Tyr Leu Asn Ile Asp Asn Ile Ser Asp Glu Ser Tyr Arg Val
    1175                1180                1185
Tyr Val Leu Val Asn Ser Lys Glu Ile Gln Thr Gln Leu Phe Leu
    1190                1195                1200
Ala Pro Ile Asn Asp Asp Pro Thr Phe Tyr Asp Val Leu Gln Ile
    1205                1210                1215
Lys Lys Tyr Tyr Glu Lys Thr Thr Tyr Asn Cys Gln Ile Leu Cys
    1220                1225                1230
Glu Lys Asp Thr Lys Thr Phe Gly Leu Phe Gly Ile Gly Lys Phe
    1235                1240                1245
Val Lys Asp Tyr Gly Tyr Val Trp Asp Thr Tyr Asp Asn Tyr Phe
    1250                1255                1260
Cys Ile Ser Gln Trp Tyr Leu Arg Arg Ile Ser Glu Asn Ile Asn
    1265                1270                1275
Lys Leu Arg Leu Gly Cys Asn Trp Gln Phe Ile Pro Val Asp Glu
    1280                1285                1290
Gly Trp Thr Glu
    1295
```

<210> SEQ ID NO 15
<211> LENGTH: 4400
<212> TYPE: DNA
<213> ORGANISM: Clostridium tetani

<400> SEQUENCE: 15

| | | | | | |
|---|---|---|---|---|---|
| tagcattaaa | aaaattagaa | cctatagtaa | ataaattaat | taatatatag | tttttataat | 60 |
| ttaattatga | ataatattct | taagataaaa | agtaaatttt | taaaaattta | aattttcagt | 120 |
| ttacaaaaaa | taacctgatt | atgttatatg | taattgtaaa | aaacatataa | aaaatcagaa | 180 |
| aaatttagga | ggtatattat | taatggatta | aataataatt | ttttaattta | cttttgatta | 240 |
| ataaatatta | aatgtttatt | ttaattagga | gatgatacgt | atgccaataa | ccataaataa | 300 |
| ttttagatat | agtgatcctg | ttaataatga | tacaattatt | atgatggagc | caccatactg | 360 |
| taagggtcta | gatatctatt | ataaggcttt | caaaataaca | gatcgtattt | ggatagtgcc | 420 |
| ggaaaggtat | gaatttggga | caaaacctga | agattttaac | ccaccatctt | cattaataga | 480 |
| aggtgcatct | gagtattacg | atccaaatta | tttaaggact | gattctgata | aagatagatt | 540 |
| tttacaaacc | atggtaaaac | tgtttaacag | aattaaaaac | aatgtagcag | gtgaagcctt | 600 |
| attagataag | ataataaatg | ccataccttta | ccttggaaat | tcatattcct | tactagacaa | 660 |
| gtttgataca | aactctaatt | cagtatcttt | taatttatta | gaacaagacc | ccagtggagc | 720 |
| aactacaaaa | tcagcaatgc | tgacaaattt | aataatattt | ggacctgggc | ctgttttaaa | 780 |
| taaaaatgag | gttagaggta | ttgtattgag | ggtagataat | aaaaattact | tcccatgtag | 840 |
| agatggtttt | ggctcaataa | tgcaaatggc | attttgccca | gaatatgtac | ctacctttga | 900 |
| taatgtaata | gaaaatatta | cgtcactcac | tattggcaaa | agcaaatatt | ttcaagatcc | 960 |
| agcattacta | ttaatgcacg | aacttataca | tgtactacat | ggtttatacg | gaatgcaggt | 1020 |
| atcaagccat | gaaattattc | catccaaaca | agaaatttat | atgcagcata | catatccaat | 1080 |
| aagtgctgaa | gaactattca | cttttggcgg | acaggatgct | aatcttataa | gtattgatat | 1140 |
| aaaaaacgat | ttatatgaaa | aaactttaaa | tgattataaa | gctatagcta | acaaacttag | 1200 |
| tcaagtcact | agctgcaatg | atcccaacat | tgatattgat | agctacaaac | aaatatatca | 1260 |
| acaaaaatat | caattcgata | agatagcaa | tggacaatat | attgtaaatg | aggataaatt | 1320 |
| tcagatacta | tataatagca | taatgtatgg | ttttacagag | attgaattgg | gaaaaaaatt | 1380 |
| taatataaaa | actagacttt | cttatttttag | tatgaatcat | gaccctgtaa | aaattccaaa | 1440 |
| tttattagat | gatacaattt | acaatgatac | agaaggattt | aatatagaaa | gcaaagatct | 1500 |
| gaaatctgaa | tataaaggac | aaaatatgag | ggtaaataca | aatgctttta | gaaatgttga | 1560 |
| tggatcaggc | ctagtttcaa | aacttattgg | cttatgtaaa | aaaattatac | caccaacaaa | 1620 |
| tataagagaa | aatttatata | atagaactgc | atcattaaca | gatttaggag | gagaattatg | 1680 |
| tataaaaatt | aaaaatgaag | atttaactttt | tatagctgaa | aaaaatagct | tttcagaaga | 1740 |
| accatttcaa | gatgaaatag | ttagttataa | tacaaaaaat | aaaccattaa | atttttaatta | 1800 |
| ttcgctagat | aaaattattg | tagattataa | tctacaaagt | aaaattacat | tacctaatga | 1860 |
| taggacaacc | ccagttacaa | aaggaattcc | atatgctcca | gaatataaaa | gtaatgctgc | 1920 |
| aagtacaata | gaaatacata | atattgatga | caatacaata | tatcaatatt | tgtatgctca | 1980 |
| aaaatctcct | acaactctac | aaagaataac | tatgactaat | tctgttgatg | acgcattaat | 2040 |
| aaattccacc | aaaatatatt | catattttcc | atctgtaatc | agtaaagtta | accaaggtgc | 2100 |
| acaaggaatt | ttattcttac | agtgggtgag | agatataatt | gatgattttta | ccaatgaatc | 2160 |

| | | |
|---|---|---|
| ttcacaaaaa actactattg ataaaatttc agatgtatcc actattgttc cttatatagg | 2220 |
| acccgcatta acattgtaa aacaaggcta tgagggaaac tttataggcg ctttagaaac | 2280 |
| taccggagtg gttttattat tagaatatat tccagaaatt actttaccag taattgcagc | 2340 |
| tttatctata gcagaaagta gcacacaaaa agaaaagata ataaaaacaa tagataactt | 2400 |
| tttagaaaaa agatatgaaa aatggattga agtatataaa ctagtaaaag caaaatggtt | 2460 |
| aggcacagtt aatacgcaat tccaaaaaag aagttatcaa atgtatagat ctttagaata | 2520 |
| tcaagtagat gcaataaaaa aaataataga ctatgaatat aaaatatatt caggacctga | 2580 |
| taaggaacaa attgccgacg aaattaataa tctgaaaaac aaacttgaag aaaaggctaa | 2640 |
| taaagcaatg ataaacataa atatatttat gagggaaagt tctagatcat tttttagttaa | 2700 |
| tcaaatgatt aacgaagcta aaaagcagtt attagagttt gatactcaaa gcaaaaatat | 2760 |
| tttaatgcag tatataaaag caaattctaa atttataggt ataactgaac taaaaaaatt | 2820 |
| agaatcaaaa ataaacaaag ttttttcaac accaattcca ttttcttatt ctaaaaatct | 2880 |
| ggattgttgg gttgataatg aagaagatat agatgttata ttaaaaaaga gtacaatttt | 2940 |
| aaatttagat attaataatg atattatatc agatatatct gggtttaatt catctgtaat | 3000 |
| aacatatcca gatgctcaat tggtgcccgg aataaatggc aaagcaatac atttagtaaa | 3060 |
| caatgaatct tctgaagtta tagtgcataa agctatggat attgaatata atgatatgtt | 3120 |
| taataatttt accgttagct tttggttgag ggttcctaaa gtatctgcta gtcatttaga | 3180 |
| acaatatggc acaaatgagt attcaataat tagctctatg aaaaaacata gtctatcaat | 3240 |
| aggatctggt tggagtgtat cacttaaagg taataactta atatggactt taaaagattc | 3300 |
| cgcgggagaa gttagacaaa taacttttag ggatttacct gataaattta atgcttattt | 3360 |
| agcaaataaa tgggtttta taactattac taatgataga ttatcttctg ctaatttgta | 3420 |
| tataaatgga gtacttatgg gaagtgcaga aattactggt ttaggagcta ttagagagga | 3480 |
| taataatata acattaaaac tagatagatg taataataat aatcaatacg tttctattga | 3540 |
| taaatttagg atattttgca aagcattaaa tccaaaagag attgaaaaat tatacacaag | 3600 |
| ttatttatct ataacctttt taagagactt ctggggaaac cctttacgat atgatacaga | 3660 |
| atattattta ataccagtag cttctagttc taaagatgtt caattgaaaa atataacaga | 3720 |
| ttatatgtat ttgacaaatg cgccatcgta tactaacgga aaattgaata tatattatag | 3780 |
| aaggttatat aatggactaa aatttattat aaaaagatat acacctaata atgaaataga | 3840 |
| ttcttttgtt aaatcaggtg attttattaa attatatgta tcatataaca ataatgagca | 3900 |
| cattgtaggt tatccgaaag atggaaatgc ctttaataat cttgatagaa ttctaagagt | 3960 |
| aggttataat gccccaggta tccctctttta taaaaaaatg gaagcagtaa aattgcgtga | 4020 |
| tttaaaaacc tattctgtac aacttaaatt atatgatgat aaaaatgcat ctttaggact | 4080 |
| agtaggtacc cataatggtc aaataggcaa cgatccaaat agggatatat taattgcaag | 4140 |
| caactggtac tttaatcatt taaaagataa aatttttagga tgtgattggt actttgtacc | 4200 |
| tacagatgaa ggatggacaa atgattaaac agattgatat gttcatgatt actctatata | 4260 |
| aaaaattaaa taatataaca atctagctat attattttg attattttct taatatatac | 4320 |
| taataaaata atcaaaatag agcctatctt aaattactga agggctgtgt caaaataaga | 4380 |
| ttttgacaca gcctctactt | 4400 |

<210> SEQ ID NO 16
<211> LENGTH: 1447

```
<212> TYPE: PRT
<213> ORGANISM: Clostridium tetani

<400> SEQUENCE: 16
```

| | | | | | | | | | | | | | | |
|---|---|---|---|---|---|---|---|---|---|---|---|---|---|---|

Ser Ile Lys Lys Ile Arg Thr Tyr Ser Ile Asn Tyr Ile Val Phe Ile
1               5                   10                  15

Ile Leu Ile Ile Phe Leu Arg Lys Val Asn Phe Lys Phe Lys Phe Ser
            20                  25                  30

Val Tyr Lys Lys Pro Asp Tyr Val Ile Cys Asn Cys Lys Lys His Ile
        35                  40                  45

Lys Asn Gln Lys Asn Leu Gly Gly Ile Leu Met Asp Ile Ile Ile
    50                  55                  60

Phe Phe Thr Phe Asp Ile Leu Asn Val Tyr Phe Asn Glu Met Ile Arg
65              70                  75                      80

Met Pro Ile Thr Ile Asn Asn Phe Arg Tyr Ser Asp Pro Val Asn Asn
                85                  90                  95

Asp Thr Ile Ile Met Met Glu Pro Pro Tyr Cys Lys Gly Leu Asp Ile
                100                 105                 110

Tyr Tyr Lys Ala Phe Lys Ile Thr Asp Arg Ile Trp Ile Val Pro Glu
            115                 120                 125

Arg Tyr Glu Phe Gly Thr Lys Pro Glu Asp Phe Asn Pro Pro Ser Ser
        130                 135                 140

Leu Ile Glu Gly Ala Ser Glu Tyr Tyr Asp Pro Asn Tyr Leu Arg Thr
145                 150                 155                 160

Asp Ser Asp Lys Asp Arg Phe Leu Gln Thr Met Val Lys Leu Phe Asn
                165                 170                 175

Arg Ile Lys Asn Asn Val Ala Gly Glu Ala Leu Leu Asp Lys Ile Ile
            180                 185                 190

Asn Ala Ile Pro Tyr Leu Gly Asn Ser Tyr Ser Leu Leu Asp Lys Phe
        195                 200                 205

Asp Thr Asn Ser Asn Ser Val Ser Phe Asn Leu Leu Glu Gln Asp Pro
    210                 215                 220

Ser Gly Ala Thr Thr Lys Ser Ala Met Leu Thr Asn Leu Ile Ile Phe
225                 230                 235                 240

Gly Pro Gly Pro Val Leu Asn Lys Asn Glu Val Arg Gly Ile Val Leu
                245                 250                 255

Arg Val Asp Asn Lys Asn Tyr Phe Pro Cys Arg Asp Gly Phe Gly Ser
                260                 265                 270

Ile Met Gln Met Ala Phe Cys Pro Glu Tyr Val Pro Thr Phe Asp Asn
            275                 280                 285

Val Ile Glu Asn Ile Thr Ser Leu Thr Ile Gly Lys Ser Lys Tyr Phe
290                 295                 300

Gln Asp Pro Ala Leu Leu Leu Met His Glu Leu Ile His Val Leu His
305                 310                 315                 320

Gly Leu Tyr Gly Met Gln Val Ser His Glu Ile Ile Pro Ser Lys
            325                 330                 335

Gln Glu Ile Tyr Met Gln His Thr Tyr Pro Ile Ser Ala Glu Glu Leu
            340                 345                 350

Phe Thr Phe Gly Gly Gln Asp Ala Asn Leu Ile Ser Ile Asp Ile Lys
        355                 360                 365

Asn Asp Leu Tyr Glu Lys Thr Leu Asn Asp Tyr Lys Ala Ile Ala Asn
    370                 375                 380

Lys Leu Ser Gln Val Thr Ser Cys Asn Asp Pro Asn Ile Asp Ile Asp
385                 390                 395                 400

-continued

```
Ser Tyr Lys Gln Ile Tyr Gln Gln Lys Tyr Gln Phe Asp Lys Asp Ser
            405                 410                 415

Asn Gly Gln Tyr Ile Val Asn Glu Asp Lys Phe Gln Ile Leu Tyr Asn
        420                 425                 430

Ser Ile Met Tyr Gly Phe Thr Glu Ile Glu Leu Gly Lys Lys Phe Asn
        435                 440                 445

Ile Lys Thr Arg Leu Ser Tyr Phe Ser Met Asn His Asp Pro Val Lys
        450                 455                 460

Ile Pro Asn Leu Leu Asp Asp Thr Ile Tyr Asn Asp Thr Glu Gly Phe
465                 470                 475                 480

Asn Ile Glu Ser Lys Asp Leu Lys Ser Glu Tyr Lys Gly Gln Asn Met
            485                 490                 495

Arg Val Asn Thr Asn Ala Phe Arg Asn Val Asp Gly Ser Gly Leu Val
            500                 505                 510

Ser Lys Leu Ile Gly Leu Cys Lys Lys Ile Ile Pro Pro Thr Asn Ile
        515                 520                 525

Arg Glu Asn Leu Tyr Asn Arg Thr Ala Ser Leu Thr Asp Leu Gly Gly
        530                 535                 540

Glu Leu Cys Ile Lys Ile Lys Asn Glu Asp Leu Thr Phe Ile Ala Glu
545                 550                 555                 560

Lys Asn Ser Phe Ser Glu Glu Pro Phe Gln Asp Glu Ile Val Ser Tyr
                565                 570                 575

Asn Thr Lys Asn Lys Pro Leu Asn Phe Asn Tyr Ser Leu Asp Lys Ile
            580                 585                 590

Ile Val Asp Tyr Asn Leu Gln Ser Lys Ile Thr Leu Pro Asn Asp Arg
        595                 600                 605

Thr Thr Pro Val Thr Lys Gly Ile Pro Tyr Ala Pro Glu Tyr Lys Ser
        610                 615                 620

Asn Ala Ala Ser Thr Ile Glu Ile His Asn Ile Asp Asp Asn Thr Ile
625                 630                 635                 640

Tyr Gln Tyr Leu Tyr Ala Gln Lys Ser Pro Thr Thr Leu Gln Arg Ile
                645                 650                 655

Thr Met Thr Asn Ser Val Asp Asp Ala Leu Ile Asn Ser Thr Lys Ile
            660                 665                 670

Tyr Ser Tyr Phe Pro Ser Val Ile Ser Lys Val Asn Gln Gly Ala Gln
        675                 680                 685

Gly Ile Leu Phe Leu Gln Trp Val Arg Asp Ile Ile Asp Asp Phe Thr
690                 695                 700

Asn Glu Ser Ser Gln Lys Thr Thr Ile Asp Lys Ile Ser Asp Val Ser
705                 710                 715                 720

Thr Ile Val Pro Tyr Ile Gly Pro Ala Leu Asn Ile Val Lys Gln Gly
                725                 730                 735

Tyr Glu Gly Asn Phe Ile Gly Ala Leu Glu Thr Thr Gly Val Val Leu
            740                 745                 750

Leu Leu Glu Tyr Ile Pro Glu Ile Thr Leu Pro Val Ile Ala Ala Leu
        755                 760                 765

Ser Ile Ala Glu Ser Ser Thr Gln Lys Glu Lys Ile Ile Lys Thr Ile
770                 775                 780

Asp Asn Phe Leu Glu Lys Arg Tyr Glu Lys Trp Ile Glu Val Tyr Lys
785                 790                 795                 800

Leu Val Lys Ala Lys Trp Leu Gly Thr Val Asn Thr Gln Phe Gln Lys
                805                 810                 815

Arg Ser Tyr Gln Met Tyr Arg Ser Leu Glu Tyr Gln Val Asp Ala Ile
            820                 825                 830
```

```
Lys Lys Ile Ile Asp Tyr Glu Tyr Lys Ile Tyr Ser Gly Pro Asp Lys
        835                 840                 845

Glu Gln Ile Ala Asp Glu Ile Asn Asn Leu Lys Asn Lys Leu Glu Glu
850                 855                 860

Lys Ala Asn Lys Ala Met Ile Asn Ile Asn Ile Phe Met Arg Glu Ser
865                 870                 875                 880

Ser Arg Ser Phe Leu Val Asn Gln Met Ile Asn Glu Ala Lys Lys Gln
            885                 890                 895

Leu Leu Glu Phe Asp Thr Gln Ser Lys Asn Ile Leu Met Gln Tyr Ile
            900                 905                 910

Lys Ala Asn Ser Lys Phe Ile Gly Ile Thr Glu Leu Lys Lys Leu Glu
            915                 920                 925

Ser Lys Ile Asn Lys Val Phe Ser Thr Pro Ile Pro Phe Ser Tyr Ser
            930                 935                 940

Lys Asn Leu Asp Cys Trp Val Asp Asn Glu Glu Asp Ile Asp Val Ile
945                 950                 955                 960

Leu Lys Lys Ser Thr Ile Leu Asn Leu Asp Ile Asn Asn Asp Ile Ile
                965                 970                 975

Ser Asp Ile Ser Gly Phe Asn Ser Ser Val Ile Thr Tyr Pro Asp Ala
            980                 985                 990

Gln Leu Val Pro Gly Ile Asn Gly  Lys Ala Ile His Leu  Val Asn Asn
            995                 1000                1005

Glu Ser  Ser Glu Val Ile Val  His Lys Ala Met Asp  Ile Glu Tyr
    1010                1015                    1020

Asn Asp  Met Phe Asn Asn Phe  Thr Val Ser Phe Trp  Leu Arg Val
    1025                1030                    1035

Pro Lys  Val Ser Ala Ser His  Leu Glu Gln Tyr Gly  Thr Asn Glu
    1040                1045                    1050

Tyr Ser  Ile Ile Ser Ser Met  Lys Lys His Ser Leu  Ser Ile Gly
    1055                1060                    1065

Ser Gly  Trp Ser Val Ser Leu  Lys Gly Asn Asn Leu  Ile Trp Thr
    1070                1075                    1080

Leu Lys  Asp Ser Ala Gly Glu  Val Arg Gln Ile Thr  Phe Arg Asp
    1085                1090                    1095

Leu Pro  Asp Lys Phe Asn Ala  Tyr Leu Ala Asn Lys  Trp Val Phe
    1100                1105                    1110

Ile Thr  Ile Thr Asn Asp Arg  Leu Ser Ser Ala Asn  Leu Tyr Ile
    1115                1120                    1125

Asn Gly  Val Leu Met Gly Ser  Ala Glu Ile Thr Gly  Leu Gly Ala
    1130                1135                    1140

Ile Arg  Glu Asp Asn Asn Ile  Thr Leu Lys Leu Asp  Arg Cys Asn
    1145                1150                    1155

Asn Asn  Asn Gln Tyr Val Ser  Ile Asp Lys Phe Arg  Ile Phe Cys
    1160                1165                    1170

Lys Ala  Leu Asn Pro Lys Glu  Ile Glu Lys Leu Tyr  Thr Ser Tyr
    1175                1180                    1185

Leu Ser  Ile Thr Phe Leu Arg  Asp Phe Trp Gly Asn  Pro Leu Arg
    1190                1195                    1200

Tyr Asp  Thr Glu Tyr Tyr Leu  Ile Pro Val Ala Ser  Ser Ser Lys
    1205                1210                    1215

Asp Val  Gln Leu Lys Asn Ile  Thr Asp Tyr Met Tyr  Leu Thr Asn
    1220                1225                    1230

Ala Pro  Ser Tyr Thr Asn Gly  Lys Leu Asn Ile Tyr  Tyr Arg Arg
```

```
                      1235                1240                1245

Leu Tyr  Asn Gly Leu Lys Phe  Ile Ile Lys Arg Tyr  Thr Pro Asn
        1250                1255                1260

Asn Glu  Ile Asp Ser Phe Val  Lys Ser Gly Asp Phe  Ile Lys Leu
        1265                1270                1275

Tyr Val  Ser Tyr Asn Asn Asn  Glu His Ile Val Gly  Tyr Pro Lys
        1280                1285                1290

Asp Gly  Asn Ala Phe Asn Asn  Leu Asp Arg Ile Leu  Arg Val Gly
        1295                1300                1305

Tyr Asn  Ala Pro Gly Ile Pro  Leu Tyr Lys Lys Met  Glu Ala Val
        1310                1315                1320

Lys Leu  Arg Asp Leu Lys Thr  Tyr Ser Val Gln Leu  Lys Leu Tyr
        1325                1330                1335

Asp Asp  Lys Asn Ala Ser Leu  Gly Leu Val Gly Thr  His Asn Gly
        1340                1345                1350

Gln Ile  Gly Asn Asp Pro Asn  Arg Asp Ile Leu Ile  Ala Ser Asn
        1355                1360                1365

Trp Tyr  Phe Asn His Leu Lys  Asp Lys Ile Leu Gly  Cys Asp Trp
        1370                1375                1380

Tyr Phe  Val Pro Thr Asp Glu  Gly Trp Thr Asn Asp  Thr Asp Tyr
        1385                1390                1395

Val His  Asp Tyr Ser Ile Lys  Ile Lys Tyr Asn Asn  Leu Ala Ile
        1400                1405                1410

Leu Phe  Leu Ile Ile Phe Leu  Ile Tyr Thr Asn Lys  Ile Ile Lys
        1415                1420                1425

Ile Glu  Pro Ile Leu Asn Tyr  Arg Ala Val Ser Lys  Asp Phe Asp
        1430                1435                1440

Thr Ala  Ser Thr
        1445

<210> SEQ ID NO 17
<211> LENGTH: 31
<212> TYPE: PRT
<213> ORGANISM: Clostridium botulinum

<400> SEQUENCE: 17

Lys Leu Leu Cys Val Arg Gly Ile Ile Thr Ser Lys Thr Lys Ser Leu
1               5                   10                  15

Asp Lys Gly Tyr Asn Lys Ala Leu Asn Asp Leu Cys Ile Lys Val
                20                  25                  30

<210> SEQ ID NO 18
<211> LENGTH: 16
<212> TYPE: PRT
<213> ORGANISM: Clostridium botulinum

<400> SEQUENCE: 18

Ile Gln Met Cys Lys Ser Val Lys Ala Pro Gly Ile Cys Ile Asp Val
1               5                   10                  15

<210> SEQ ID NO 19
<211> LENGTH: 25
<212> TYPE: PRT
<213> ORGANISM: Clostridium botulinum

<400> SEQUENCE: 19

Thr Lys Phe Cys His Lys Ala Ile Asp Gly Arg Ser Leu Tyr Asn Lys
1               5                   10                  15
```

-continued

Thr Leu Asp Cys Arg Glu Leu Leu Val
            20                  25

<210> SEQ ID NO 20
<211> LENGTH: 20
<212> TYPE: PRT
<213> ORGANISM: Clostridium botulinum

<400> SEQUENCE: 20

Thr Lys Val Cys Leu Arg Leu Thr Lys Asn Ser Arg Asp Asp Ser Thr
1               5                   10                  15

Cys Ile Lys Val
            20

<210> SEQ ID NO 21
<211> LENGTH: 21
<212> TYPE: PRT
<213> ORGANISM: Clostridium botulinum

<400> SEQUENCE: 21

Ile Arg Phe Cys Lys Asn Ile Val Ser Val Lys Gly Ile Arg Lys Ser
1               5                   10                  15

Ile Cys Ile Glu Ile
            20

<210> SEQ ID NO 22
<211> LENGTH: 23
<212> TYPE: PRT
<213> ORGANISM: Clostridium botulinum

<400> SEQUENCE: 22

Val Lys Phe Cys Lys Ser Val Ile Pro Arg Lys Gly Thr Lys Ala Pro
1               5                   10                  15

Pro Arg Leu Cys Ile Arg Val
            20

<210> SEQ ID NO 23
<211> LENGTH: 21
<212> TYPE: PRT
<213> ORGANISM: Clostridium botulinum

<400> SEQUENCE: 23

Ile Ala Met Cys Lys Pro Val Met Tyr Lys Asn Thr Gly Lys Ser Glu
1               5                   10                  15

Gln Cys Ile Ile Val
            20

<210> SEQ ID NO 24
<211> LENGTH: 35
<212> TYPE: PRT
<213> ORGANISM: Clostridium botulinum

<400> SEQUENCE: 24

Ile Gly Leu Cys Lys Lys Ile Ile Pro Pro Thr Asn Ile Arg Glu Asn
1               5                   10                  15

Leu Tyr Asn Arg Thr Ala Ser Leu Thr Asp Leu Gly Gly Glu Leu Cys
            20                  25                  30

Ile Lys Ile
        35

<210> SEQ ID NO 25
<211> LENGTH: 7
<212> TYPE: PRT

```
<213> ORGANISM: Clostridium botulinum

<400> SEQUENCE: 25

Ala Leu Ala Pro Tyr Ile Pro
1               5

<210> SEQ ID NO 26
<211> LENGTH: 9
<212> TYPE: PRT
<213> ORGANISM: Clostridium botulinum

<400> SEQUENCE: 26

Arg Phe Met Asp Tyr Trp Glu Gly Leu
1               5

<210> SEQ ID NO 27
<211> LENGTH: 9
<212> TYPE: PRT
<213> ORGANISM: Clostridium botulinum
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 27

Phe Xaa Xaa Xaa Leu Trp Xaa Xaa Leu
1               5

<210> SEQ ID NO 28
<211> LENGTH: 14
<212> TYPE: PRT
<213> ORGANISM: Clostridium botulinum

<400> SEQUENCE: 28

Glu Leu Glu Ser Pro Pro Pro Tyr Ser Arg Tyr Pro Met
1               5                   10

<210> SEQ ID NO 29
<211> LENGTH: 7
<212> TYPE: PRT
<213> ORGANISM: Clostridium botulinum

<400> SEQUENCE: 29

Lys Val Gly Phe Phe Lys Arg
1               5

<210> SEQ ID NO 30
<211> LENGTH: 10
<212> TYPE: PRT
<213> ORGANISM: Clostridium botulinum

<400> SEQUENCE: 30

Leu Leu Val Arg Gly Arg Thr Leu Val Val
1               5                   10

<210> SEQ ID NO 31
<211> LENGTH: 10
<212> TYPE: PRT
<213> ORGANISM: Clostridium botulinum

<400> SEQUENCE: 31

Asp Arg His Asp Ser Gly Leu Asp Ser Met
1               5                   10
```

-continued

```
<210> SEQ ID NO 32
<211> LENGTH: 7
<212> TYPE: PRT
<213> ORGANISM: Clostridium botulinum
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 32

Pro Xaa Ala Xaa Val Xaa Pro
1               5

<210> SEQ ID NO 33
<211> LENGTH: 7
<212> TYPE: PRT
<213> ORGANISM: Clostridium botulinum
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 33

Pro Pro Xaa Tyr Xaa Xaa Met
1               5

<210> SEQ ID NO 34
<211> LENGTH: 5
<212> TYPE: PRT
<213> ORGANISM: Clostridium botulinum
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 34

Pro Pro Xaa Tyr Xaa
1               5
```